United States Patent [19]
Panescu et al.

[11] Patent Number: 5,848,969
[45] Date of Patent: Dec. 15, 1998

[54] SYSTEMS AND METHODS FOR VISUALIZING INTERIOR TISSUE REGIONS USING EXPANDABLE IMAGING STRUCTURES

[75] Inventors: Dorin Panescu, Sunnyvale; James G. Whayne, Saratoga; David K. Swanson, Mountain View; David McGee, Sunnyvale; Harm TenHoff, Mountain View, all of Calif.

[73] Assignee: EP Technologies, Inc., Sunnyvale, Calif.

[21] Appl. No.: 736,827

[22] Filed: Oct. 28, 1996

[51] Int. Cl.⁶ .......................................... A61B 8/00
[52] U.S. Cl. ........................ 600/462; 600/463; 600/439
[58] Field of Search ................... 128/662.06, 662.03, 128/660.1, 660.03, 642; 600/459, 446, 463, 439, 373–375; 607/122

[56] References Cited

U.S. PATENT DOCUMENTS

| | | | |
|---|---|---|---|
| 4,821,731 | 4/1989 | Martinelli et al. | 128/662.06 |
| 5,135,001 | 8/1992 | Sinofsky | 128/662.06 |
| 5,156,151 | 10/1992 | Imran | 600/375 |
| 5,190,046 | 3/1993 | Shturman | 128/662.06 |
| 5,295,484 | 3/1994 | Marcus et al. | 600/439 |
| 5,324,284 | 6/1994 | Imran | 606/15 |
| 5,325,860 | 7/1994 | Seward et al. | 600/439 |
| 5,409,000 | 4/1995 | Imran | 600/470 X |
| 5,433,198 | 7/1995 | Desai | 128/642 |
| 5,485,849 | 1/1996 | Panescu et al. | 128/699 |
| 5,513,639 | 5/1996 | Satomi et al. | 128/660.1 |

FOREIGN PATENT DOCUMENTS

| | | | |
|---|---|---|---|
| WO 90/13259 | 11/1990 | WIPO | A61B 8/12 |
| WO 95/07657 | 3/1995 | WIPO | A61B 8/12 |

*Primary Examiner*—Francis J. Jaworski
*Attorney, Agent, or Firm*—Lyon & Lyon LLP

[57] ABSTRACT

An imaging structure has a periphery adapted to selectively assume an expanded geometry and a collapsed geometry. The periphery of the imaging structure carries an array of spaced apart ultrasound transducers.

51 Claims, 10 Drawing Sheets

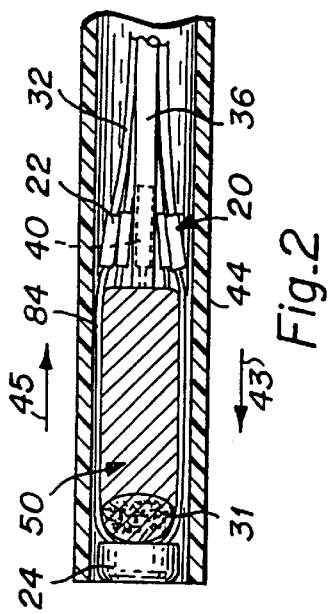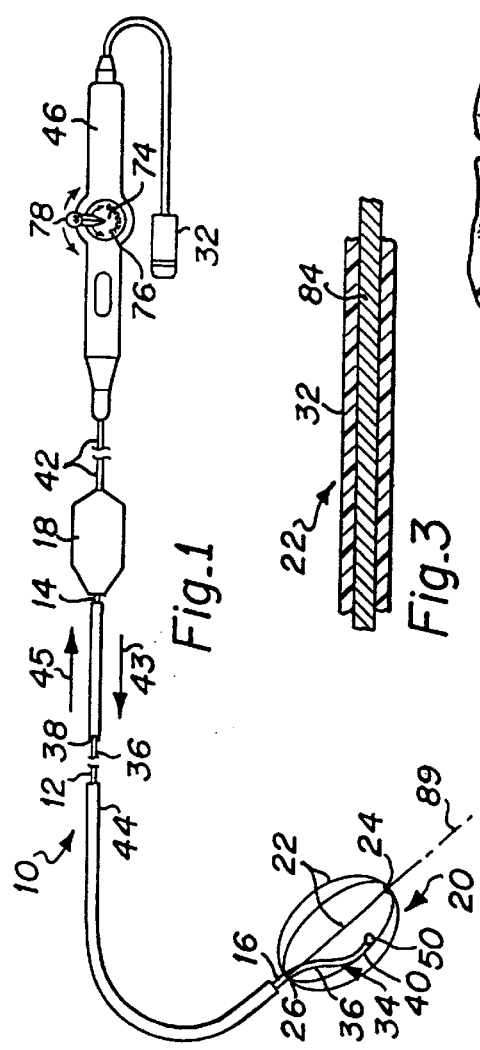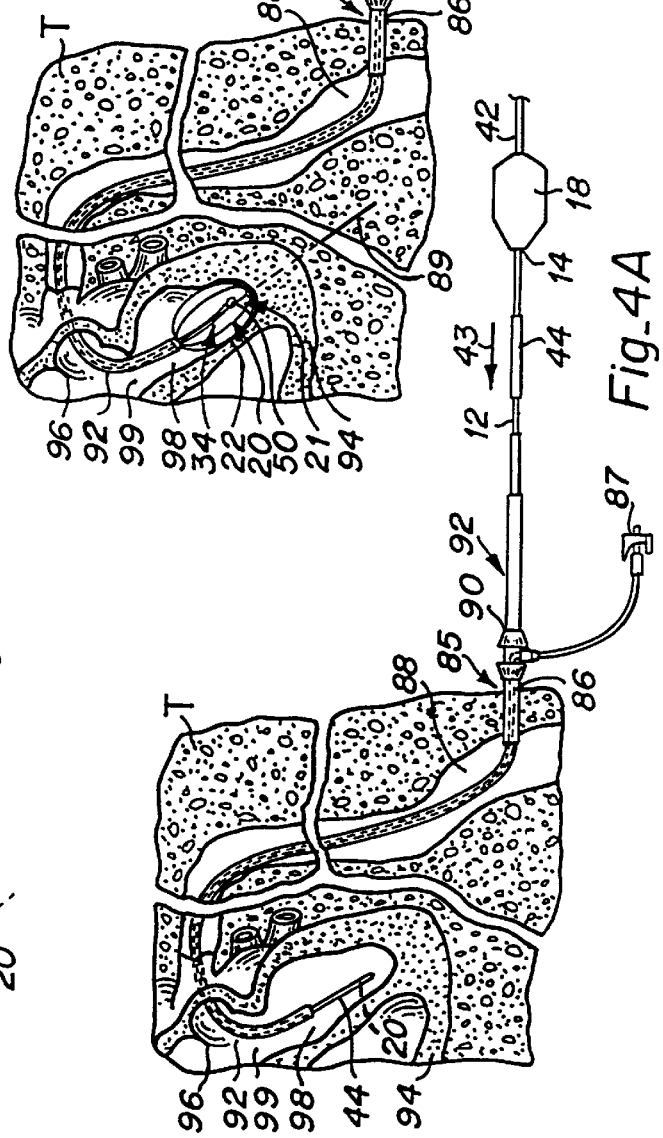

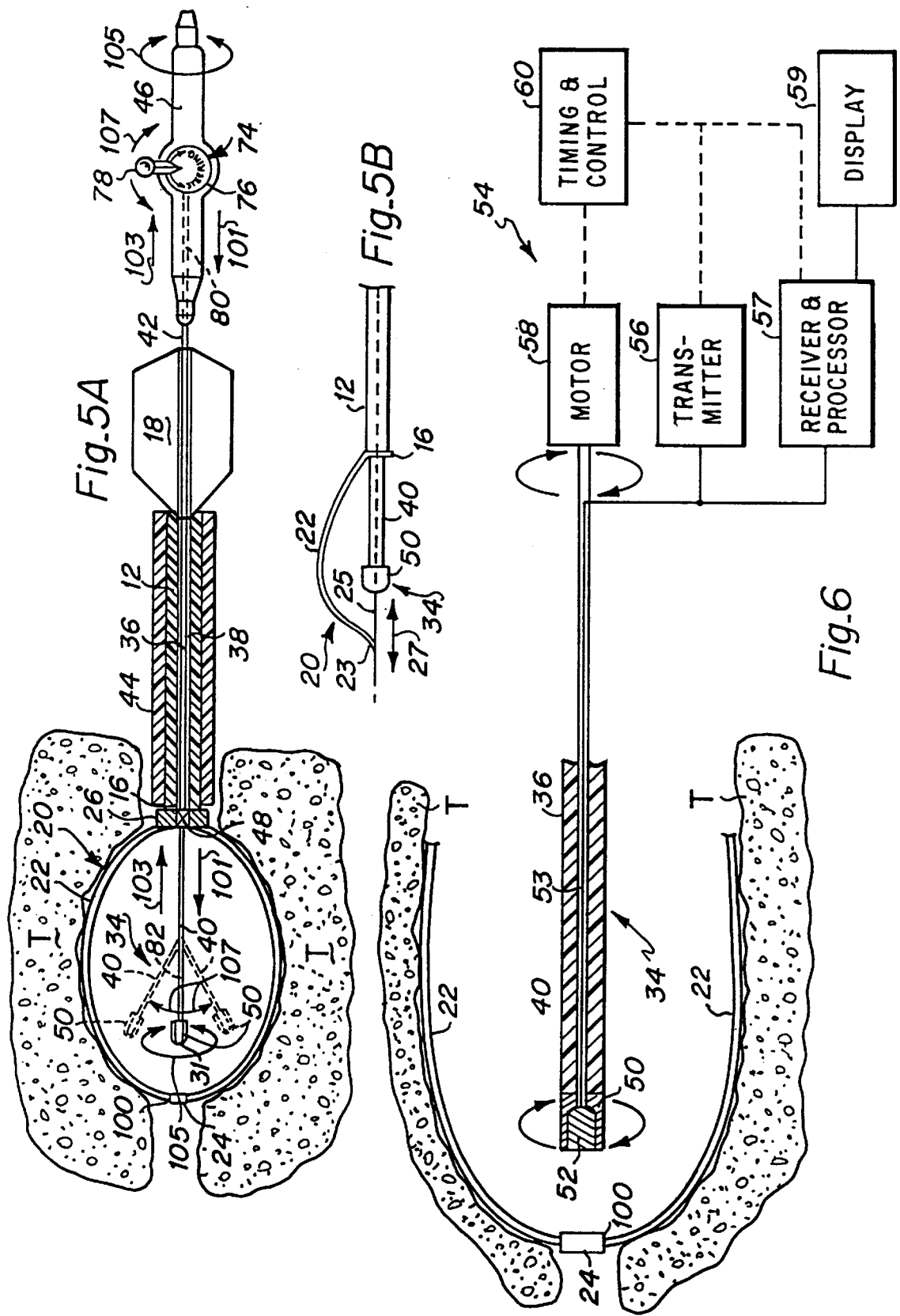

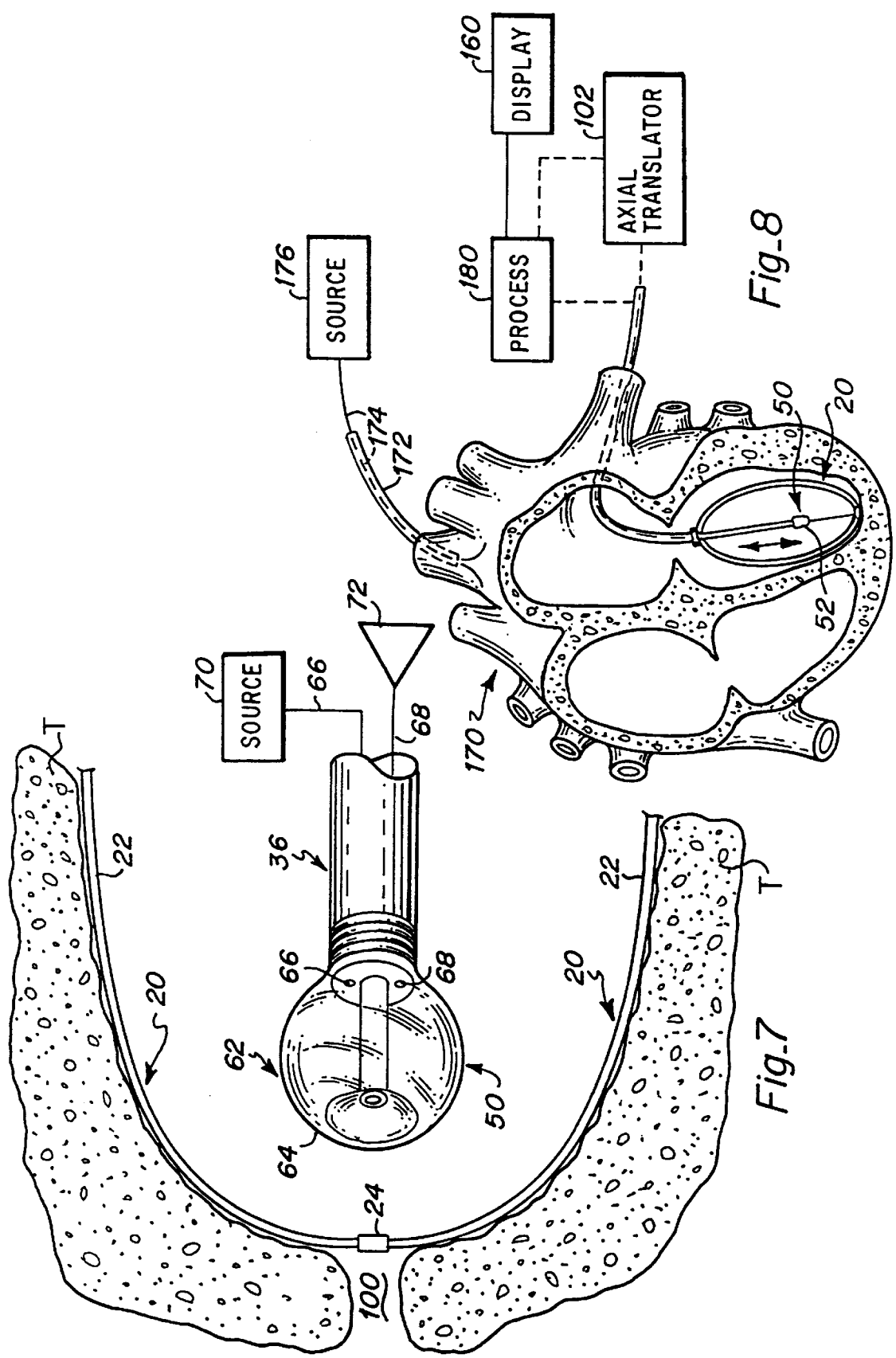

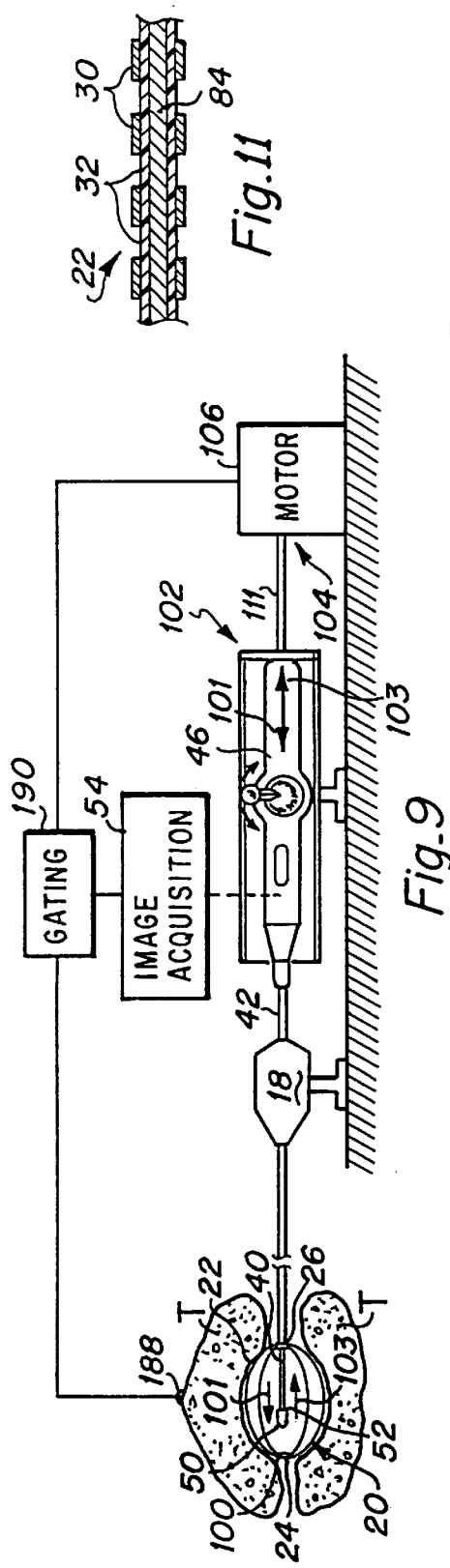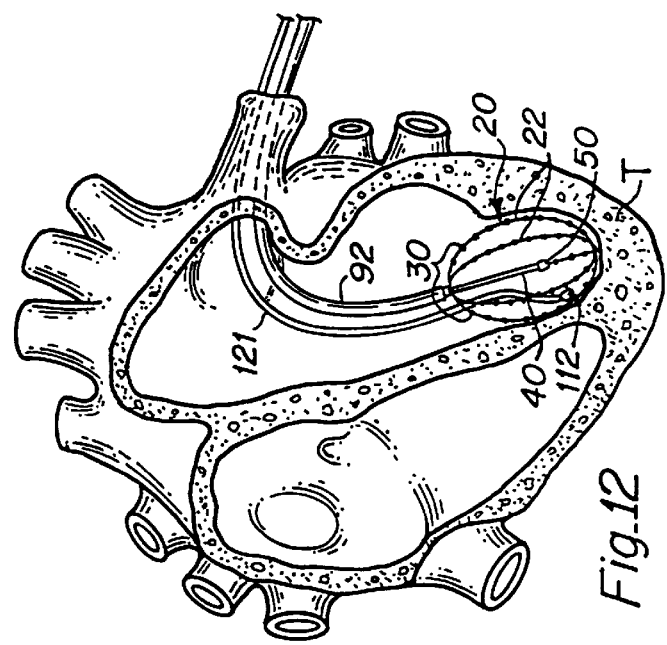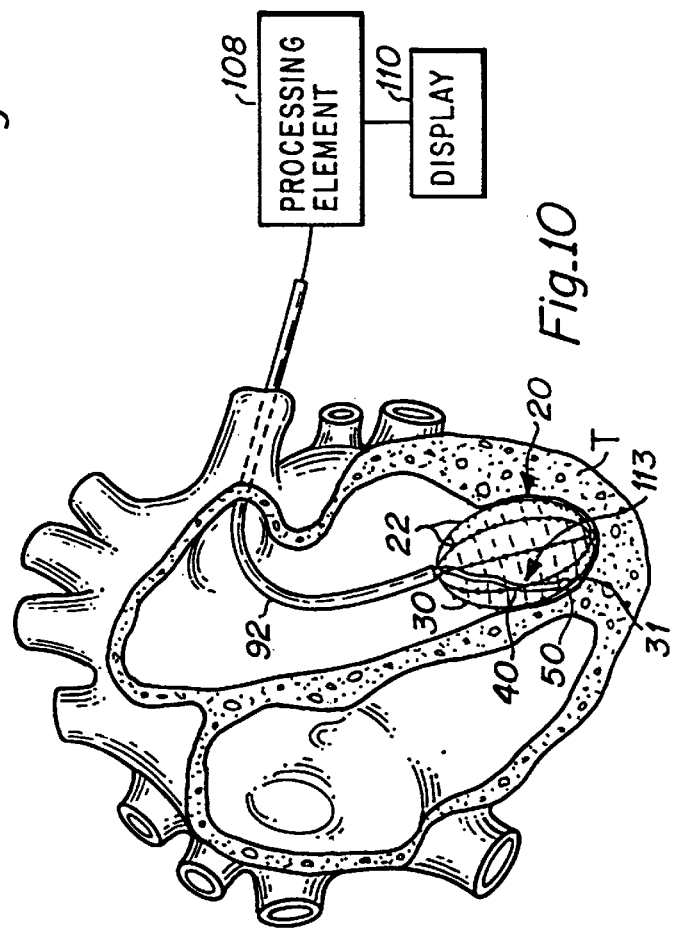

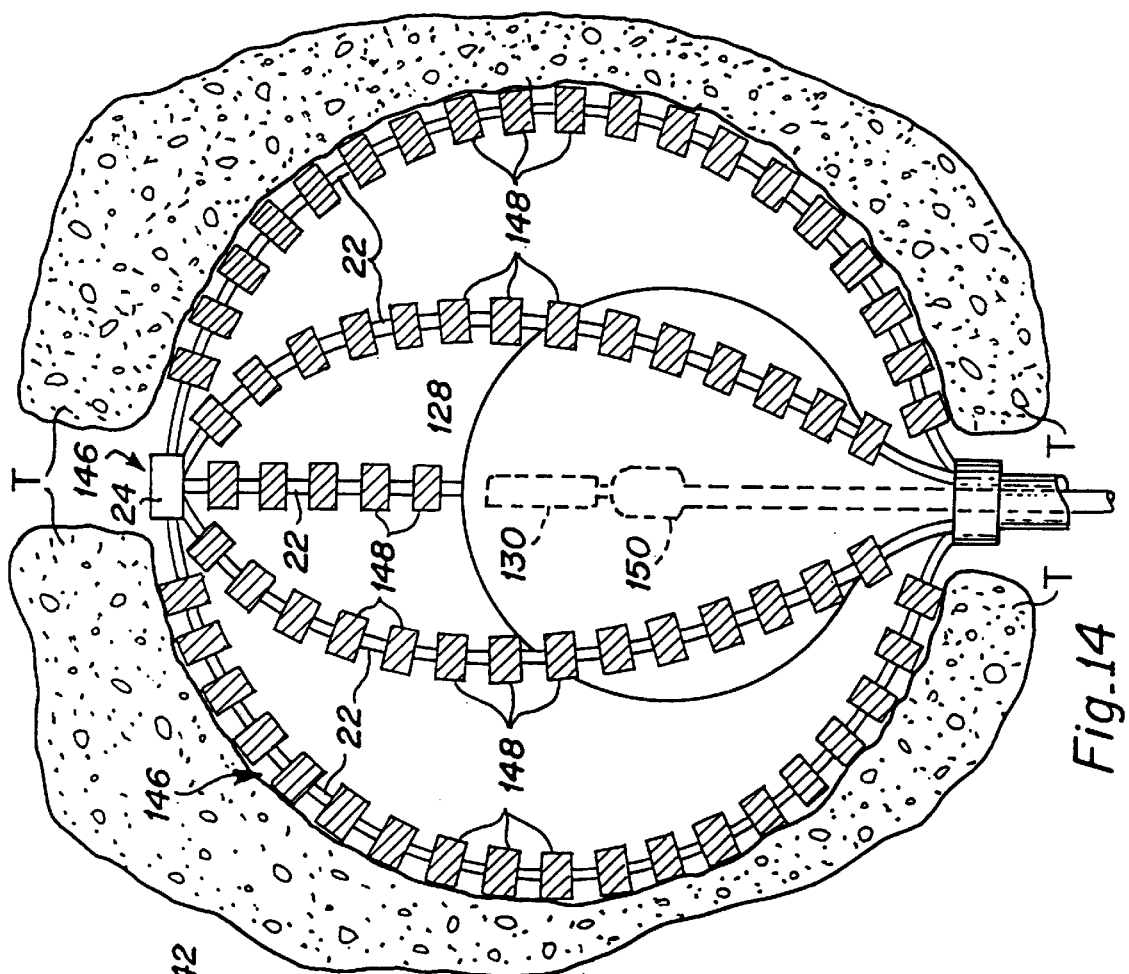
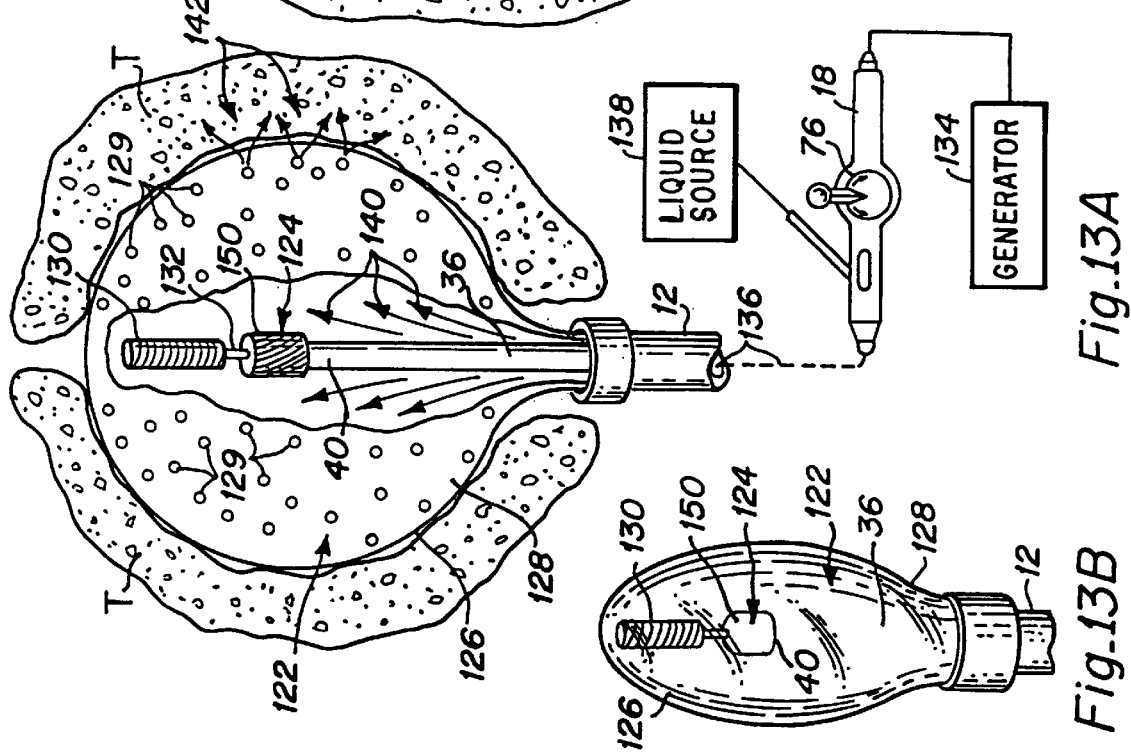
Fig. 14
Fig. 13A
Fig. 13B

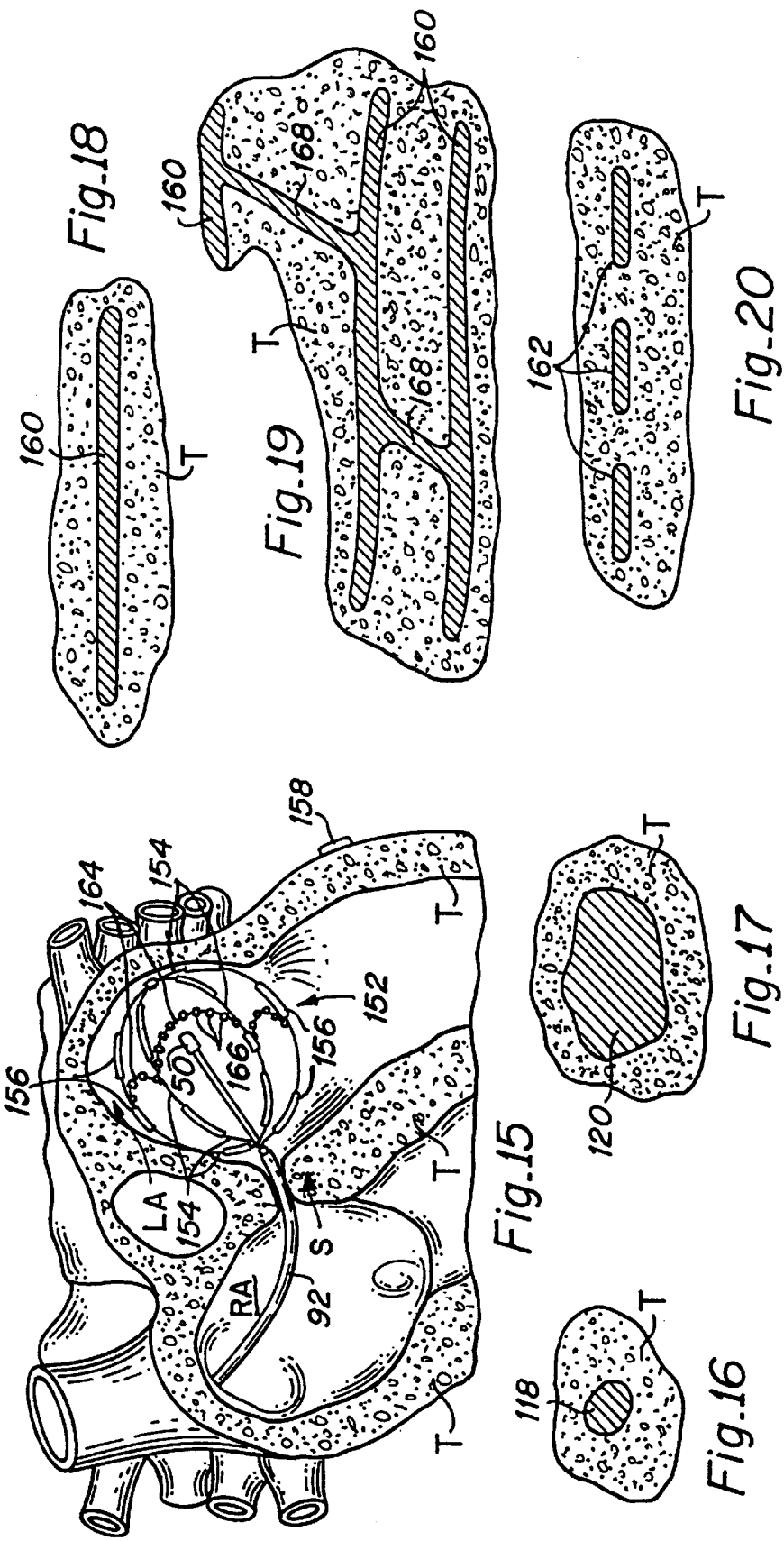

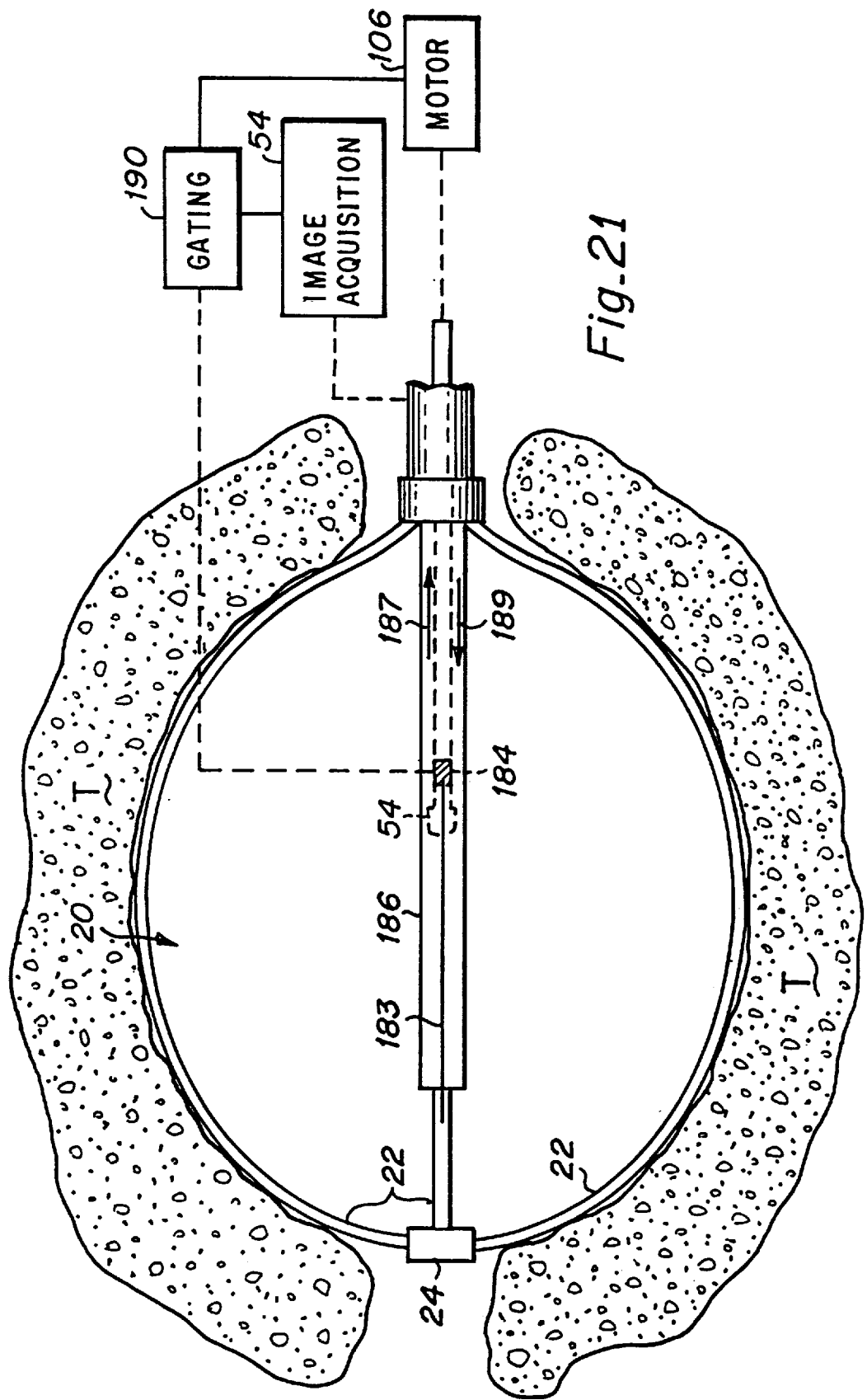

SYSTEMS AND METHODS FOR VISUALIZING INTERIOR TISSUE REGIONS USING EXPANDABLE IMAGING STRUCTURES

FIELD OF THE INVENTION

In a general sense, the invention is directed to systems and methods for visualizing interior regions of the human body. In a more particular sense, the invention is directed to systems and methods for mapping or ablating heart tissue for treating cardiac conditions.

BACKGROUND OF THE INVENTION

Systems and methods for visualizing interior regions of a living body are known. For example, ultrasound systems and methods are shown and described in Yock U.S. Pat. Nos. 5,313,949 and Webler et al. 5,485,846.

Due to dynamic forces within the body, it can be difficult to stabilize internal imaging devices to consistently generate accurate images having the quality required to prescribe appropriate treatment or therapy. There is often an attendant need to constantly position and reposition the image acquisition element. In addition, tissue and anatomic structures inside the body can contact and occlude the image acquisition element.

External imaging modalities are available. Still, these alternative modalities have their own shortcomings.

For example, in carrying out endocardial ablation procedures, fluoroscopic imaging is widely used to identify anatomic landmarks within the heart. Fluoroscopic imaging is also widely used to locate the position of the ablation electrode or electrodes relative to the targeted ablation site. It is often difficult to identify these anatomic sites using fluoroscopy. It is also difficult, if not impossible, to use fluoroscopy to ascertain that the desired lesion pattern has been created after ablation. Often, the achievement of desired lesion characteristics must be inferred based upon measurements of applied ablation power, system impedance, tissue temperature, and ablation time. Furthermore, fluoroscopy cannot readily locate the border zones between infarcted tissue and normal tissue, where efficacious ablation zones are believed to reside.

SUMMARY OF THE INVENTION

The invention provides improved systems and methods to visualize interior body regions. The systems and methods provide an imaging structure having a periphery adapted to selectively assume an expanded geometry and a collapsed geometry. The periphery of the imaging structure carries an array of spaced apart ultrasound transducers.

In a preferred embodiment, the system and methods guide the imaging structure into the interior body region, with the imaging structure assuming the collapsed geometry. The systems and methods cause the imaging structure to assume the expanded geometry upon arrival in the interior body region. In this expanded geometry, the systems and methods operate the imaging structure to visualize tissue in the interior body region.

In a preferred embodiment, the systems and methods move the imaging structure within a support structure, which extends beyond the periphery of the imaging structure. The support structure stabilizes the imaging structure, while the imaging structure visualizes tissue in the interior body region. The support structure resists dislodgment or disorientation of the imaging structure, despite the presence of dynamic forces.

In a preferred embodiment, the array comprises a phased array of ultrasound transducers.

Other features and advantages of the inventions are set forth in the following Description and Drawings, as well as in the appended Claims.

BRIEF DESCRIPTION OF THE DRAWINGS

FIG. 1 is a plan view of a system for visualizing tissue that includes a support structure carrying an imaging probe;

FIG. 2 is a side section view of the imaging probe and support structure of FIG. 1 in a collapsed condition within an external slidable sheath;

FIG. 3 is a side section view of a portion of a spline that forms a part of the support structure shown in FIG. 1;

FIGS. 4A and 4B are side sectional, somewhat diagrammatic views of the deployment of the support structure and imaging probe shown in FIG. 1 within a heart chamber;

FIG. 5A is a side section view of the support structure and imaging probe shown in FIG. 1, showing various paths in which the imaging probe can be moved when located within a body region;

FIG. 5B is a side view of an alternative embodiment of an imaging probe and a support structure comprising a single spline element;

FIG. 6 is an enlarged view of one embodiment of the support structure and imaging probe, in which the imaging probe includes a rotating ultrasonic transducer crystal;

FIG. 7 is an enlarged view of another embodiment of the support structure and imaging probe, in which the imaging probe includes a fiber optic assembly;

FIG. 8 is a partial side section, perspective, and largely schematic, view of a support structure and imaging probe as shown in FIG. 1, in which the imaging probe is associated with a system to conduct contrast echocardiography to identify potential ablation sites by imaging tissue perfusion;

FIG. 9 is a partial side section, largely schematic view of the support structure and imaging probe shown in FIG. 1, including an electro-mechanical axial translator connected to the imaging probe;

FIG. 10 is a side section view, somewhat diagrammatic is nature, showing a support structure and imaging probe, in which both the structure and the probe carry electrodes;

FIG. 11 is a side section view of a portion of an electrode-carrying spline that forms a part of the support structure shown in FIG. 10;

FIG. 12 is a side section view of a heart and a perspective view of the support structure and imaging probe shown in FIG. 10, being used in association with a separate roving mapping, pacing, or ablating electrode;

FIG. 13A is a side view, with portions removed, of a support assembly comprising a expanded porous body capable of ionic transfer of ablation energy, which carries an interior imaging probe;

FIG. 13B is a side elevation view of the porous body shown in FIG. 13A, with the porous body shown in a collapsed condition for introduction into an interior body region;

FIG. 14 is a side view of a support assembly carrying within it the porous body and imaging probe assembly shown in FIGS. 13A and 13B;

FIG. 15 is a side view, somewhat diagrammatic in form, showing a support structure that carries within it a movable imaging probe, the support structure also carrying multiple electrodes sized to create long lesion patterns;

FIG. 16 is an illustration representative of a typical small tissue lesion pattern;

FIG. 17 is an illustration representative of a typical larger tissue lesion pattern;

FIG. 18 is an illustration representative of a typical long tissue lesion pattern;

FIG. 19 is an illustration representative of a typical complex long tissue lesion pattern;

FIG. 20 is an illustration representative of a typical segmented tissue lesion pattern;

FIG. 21 is a side section view, somewhat diagrammatic in form, showing a support structure that carries within it an image acquisition element gated according to intracardiac activation sensed by an electrode also carried by the support structure;

Figure 22:
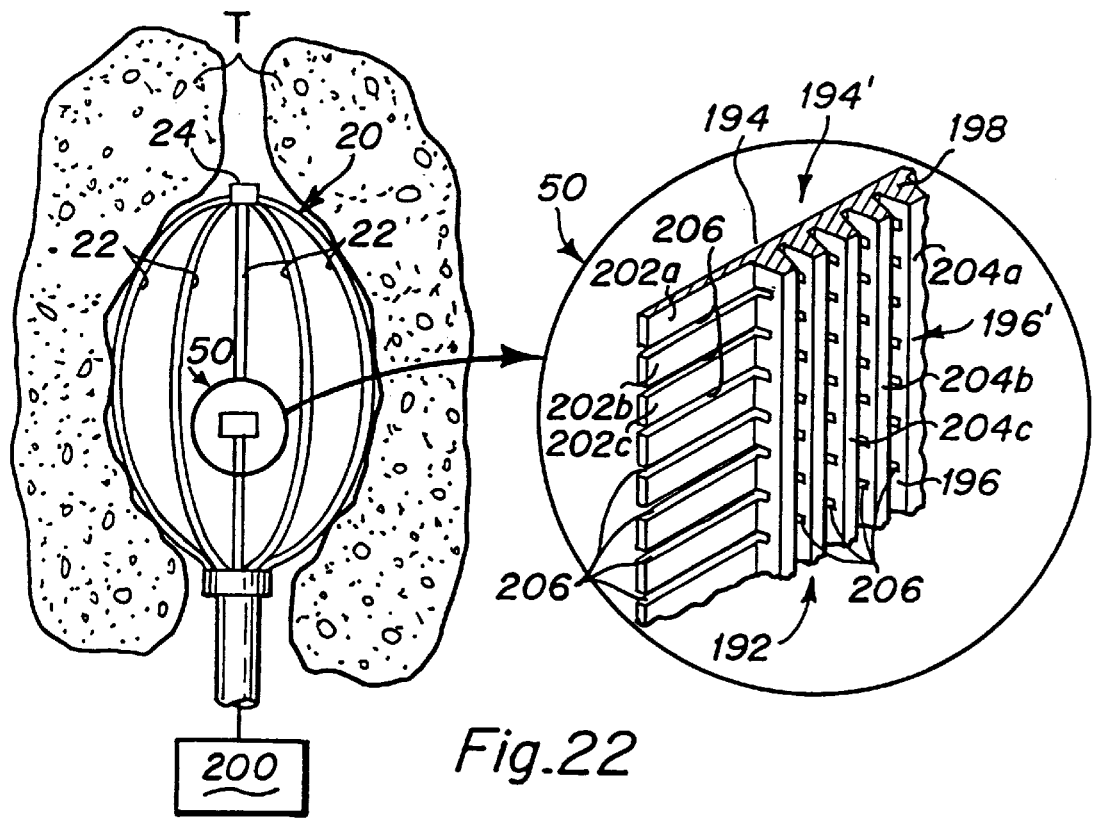
FIG. 22 is a side section view, somewhat diagrammatic in form, of a support structure that carries within it an image acquisition element, also shown with an enlarged perspective view, comprising a phased transducer array that includes multiple transducers panels scored on different planar sections of a piezoelectric material.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

FIG. 1 shows a system 10, which embodies features of the invention, for visualizing interior regions of a living body. The invention is well adapted for use inside body lumens, chambers or cavities for either diagnostic or therapeutic purposes. It particularly lends itself to catheter-based procedures, where access to the interior body region is obtained, for example, through the vascular system or alimentary canal, without complex, invasive surgical procedures.

The invention may be used in diverse body regions for diagnosing or treating diseases. For example, various aspects of the invention have application for the diagnosis and treatment of arrhythmia conditions within the heart, such as ventricular tachycardia or atrial fibrillation. The invention also has application in the diagnosis or treatment of intravascular ailments, in association, for example, with angioplasty or atherectomy techniques. Various aspects of the invention also have application for diagnosis or treatment of ailments in the gastrointestinal tract, the prostrate, brain, gall bladder, uterus, and other regions of the body. The invention can also be used in association with systems and methods that are not necessarily catheter-based. The diverse applicability of the invention in these and other fields of use will become apparent.

I. Visualization for Diagnostic Purposes

The invention makes it possible for a physician to access and visualize or image inter-body regions, to thereby locate and identify abnormalities that may be present. The invention provides a stable platform through which accurate displays of these images can be created for viewing and analysis by the physician. Accurate images enable the physician to prescribe appropriate treatment or therapy.

As implemented in the embodiment shown in FIG. 1, the invention provides a system 10 comprising a support structure 20 that carries within it an imaging or visualizing probe 34. As FIG. 1 shows, the system 10 includes a flexible catheter tube 12 with a proximal end 14 and a distal end 16. The proximal end 14 carries an attached handle 18. The distal end 16 carries the support structure 20.

A. The Support Structure

The support structure 20 can be constructed in various ways. In one preferred embodiment (illustrated in FIG. 1), the structure 20 comprises two or more flexible spline elements 22. In FIG. 1, the support structure 20 includes eight spline elements 22. Of course, fewer or more spline elements 22 can be present. For example, FIG. 5A shows the support structure 20 comprising just two, generally oppositely spaced spline elements 22. As another example, FIG. 5B shows the support structure 20 comprising a single spline element 22. In FIG. 5B, the distal end 23 of the spline element 22 is attached to a stylet 25, carried by the catheter tube 12, which moves the distal end 23 (as shown by arrows 27) along the axis of the catheter tube 12 to adjust the curvature of the spline element 22.

As FIG. 3 shows, each spline element 22 preferably comprises a flexible core body 84 enclosed within a flexible, electrically nonconductive sleeve 32. The sleeve 32 is made of, for example, a polymeric, electrically nonconductive material, like polyethylene or polyurethane. The sleeve 32 is preferable heat shrunk about the core body 84.

The core body 84 is made from resilient, inert wire or plastic. Elastic memory material such as nickel titanium (commercially available as NITINOL™ material) can be used. Resilient injection molded plastic or stainless steel can also be used. Preferably, the core body 84 is a thin, rectilinear strip. The rectilinear cross-section imparts resistance to twisting about the longitudinal axis of the core body 84, thereby providing structural stability and good biomechanical properties. Other cross-sectional configurations, such as cylindrical, can be used, if desired.

The core bodies 84 of the spline elements 22 extend longitudinally between a distal hub 24 and a base 26. The base 26 is carried by the distal end 16 of the catheter tube 12. As FIG. 1 shows, each core body 84 is preformed with a convex bias, creating a normally open three-dimensional basket structure expanded about a main center axis 89.

As FIG. 2 shows, in the illustrated and preferred embodiment, the system 10 includes an outer sheath 44 carried about the catheter tube 12. The sheath 44 has an inner diameter that is greater than the outer diameter of the catheter tube 12. As a result, the sheath 44 slides along the outside of the catheter tube 12.

Forward movement (arrow 43) advances the slidable sheath 44 over the support structure 20. In this position, the slidable sheath 44 compresses and collapses the support structure 20 into a low profile (shown in FIG. 2) for introduction through a vascular or other body passage to the intended interior site.

Rearward movement (arrow 45) retracts the slidable sheath 44 away from the support structure 20. This removes the compression force. The freed support structure 20 opens (as FIG. 1 shows) and assumes its three-dimensional shape.

(i) Deployment of the support Assembly

The methodology for deploying the support structure 20 of course varies according to the particular inter-body region targeted for access. FIGS. 4A and 4B show a representative deployment technique usable when vascular access to a heart chamber is required.

The physician uses an introducer 85, made from inert plastic materials (e.g., polyester), having a skin-piercing cannula 86. The cannula 86 establishes percutaneous access into, for example, the femoral artery 88. The exterior end of the introducer 85 includes a conventional hemostatic valve 90 to block the outflow of blood and other fluids from the access. The valve may take the form of a conventional slotted membrane or conventional shutter valve arrangement (not shown). A valve 90 suitable for use may be commercial procured from B. Braun Medical Company (Bethlehem, Pa.). The introducer 85 includes a flushing port 87 to introduce sterile saline to periodically clean the region of the valve 90.

As FIG. 4A shows, the physician advances a guide sheath 92 through the introducer 85 into the accessed artery 88. A guide catheter or guide wire (not shown) may be used in association with the guide sheath 92 to aid in directing the guide sheath 92 through the artery 88 toward the heart 94. It should be noted that the views of the heart 94 and other interior regions of the body in this Specification are not intended to be anatomically accurate in every detail. The Figures show anatomic details in diagrammatic form as necessary to show the features of the invention.

The physician observes the advancement of the guide sheath 92 through the artery 88 using fluoroscopic or ultrasound imaging, or the like. The guide sheath 92 can include a radio-opaque compound, such as barium, for this purpose. Alternatively, a radio-opaque marker can be placed at the distal end of the guide sheath 92.

In this way, the physician maneuvers the guide sheath 92 through the artery 88 retrograde past the aortic valve and into the left ventricle 98. The guide sheath 92 establishes a passageway through the artery 88 into the ventricle 98, without an invasive open heart surgical procedure. If an alternative access to the left atrium or ventricle is desired (as FIG. 15 shows), a conventional transeptal sheath assembly (not shown) can be used to gain passage through the septum between the left and right atria. Access to the right atrium or ventricle is accomplished in the same manner, but without advancing the transeptal sheath across the atrial septum.

As FIG. 4A shows, once the guide sheath 92 is placed in the targeted region, the physician advances the catheter tube 12, with the support structure 20 confined within the slidable sheath 44, through the guide sheath 92 and into the targeted region.

As FIG. 4B shows, pulling back upon the slidable sheath 44 (see arrow 45 in FIG. 4B) allows the structure 20 to spring open within the targeted region for use. When deployed for use (as FIG. 4B shows), the shape of the support structure 20 (which, in FIG. 4B, is three-dimensional) holds the spline elements 22 in intimate contact against the surrounding tissue mass. As will be explained in greater detail later (and as FIG. 4B shows), the support structure 20 has an open interior 21, which surrounds the imaging probe 34, keeping the tissue mass from contacting it.

As FIGS. 1 and 4B show, the geometry of flexible spline elements 22 is radially symmetric about the main axis 89. That is, the spline elements 22 uniformly radiate from the main axis 89 at generally equal arcuate, or circumferential, intervals.

The elements 22 also present a geometry that is axially symmetric along the main axis 89. That is, when viewed from the side (as FIGS. 1 and 4B show) the proximal and distal regions of the assembled splines 22 have essentially the same curvilinear geometry along the main axis 89.

Of course, if desired, the spline elements 22 can form various other geometries that are either radially asymmetric, or axially asymmetric, or both. In this respect, the axial geometry for the structure 20, whether symmetric or asymmetric, is selected to best conform to the expected interior contour of the body chamber that the structure 20 will, in use, occupy. For example, the interior contour of a heart ventricle differs from the interior contour of a heart atrium. The ability to provide support structures 20 with differing asymmetric shapes makes it possible to provide one discrete configuration tailored for atrial use and another discrete configuration tailored for ventricular use. Examples of asymmetric arrays of spline structures 20 for use in the heart are shown in copending U.S. application Ser. No. 08/728,698 filed Oct. 28, 1996, entitled "Asymmetric Multiple Electrode Support Structures," which is incorporated herein by reference.

B. The Imaging Probe

As FIG. 5A shows, the imaging probe 34 located within the support structure 20 includes a flexible body 36, which extends through a central bore 38 in the catheter tube 12. The body 36 has a distal region 40 that projects beyond the distal end 16 of the catheter tube 12 into the interior of the support structure 20. The body 36 also includes a proximal region 42 that carries an auxiliary handle 46. Another conventional hemostatic valve 48 is located at the distal end 16 of the catheter tube 12 to block the backflow of fluid through the catheter tube 12 while allowing the passage of the body 36.

The distal body region 40 carries an image acquisition element 50, which will be called in abbreviated form the IAE. The IAE 50 generates visualizing signals representing an image of the area, and objects and tissues that occupy the area, surrounding the structure 20. The IAE 50 can be of various constructions.

(i) Ultrasonic Imaging

In one embodiment (see FIG. 6), the IAE 50 comprises an ultrasonic transducer 52. The transducer 52 forms a part of a conventional ultrasound imaging system 54 generally of the type shown in U.S. Pat. No. 5,313,949. This patent is incorporated herein by reference.

The transducer 52 comprises one or more piezoelectric crystals formed of, for example, barium titinate or cinnabar, which is capable of operating at a frequency range of 5 to 20 megahertz. Other types of ultrasonic crystal oscillators can be used. For example, organic electrets such as polyvinylidene difluoride and vinylidene fluoride-trifluoroethylene copolymers can also be used.

The imaging system 54 includes a transmitter 56 coupled to the transducer crystal 52 (see FIG. 6). The transmitter 56 generates voltage pulses (typically in the range of 10 to 150 volts) for excitation of the transducer crystal 52. The voltage pulses cause the transducer crystal 52 to produce sonic waves.

As the transmitter 56 supplies voltage pulses to the transducer crystal 52, a motor 58 rotates the transducer crystal 52 (being linked by the flexible drive shaft 53, which passes through a bore in the tube 36). The transmission of voltage pulses (and, thus, the sonic waves) and the rotation of the transducer crystal 52 are synchronized by a timing and control element 60. Typically, the motor 58 rotates the transducer crystal 52 in the range of 500 to 2000 rpm, depending upon the frame rate of the image desired. The rotating transducer crystal 52 thereby projects the sonic waves in a 360° pattern into the interior of the chamber or cavity that surrounds it.

Tissue, including tissue forming anatomic structures, such as heart valves (which is generally designated T in the Figures), and internal tissue structures and deposits or lesions on the tissue, scanned by the rotating transducer crystal 52 will scatter the sonic waves. The support structure 20 also scatters the sonic waves. The scattered waves return to the rotating transducer crystal 52. The transducer crystal 52 converts the scattered waves into electrical signals. The imaging system 54 includes a receiver 57, which amplifies these electrical signals. The imaging system 54 digitally processes the signals, synchronized by the timing and control element 60 to the rotation of the transducer crystal 52, using known display algorithms; for example, conventional radar (PPI) algorithms. These algorithms are based upon the direct relationship that elapsed time ($\Delta t$) between pulse emission and return echo has to the distance (d) of the tissue from the transducer, expressed as follows:

$$d=\Delta t/2v$$

where v is the speed of sound in the surrounding media.

The digitally processed signals are supplied to a display unit 59. The display unit 59 comprises a screen, which can be, for example, a CRT monitor. The display screen 59 shows an ultrasound image or profile in the desired format, which depicts the tissue and anatomic structures scanned by the transducer crystal 52. The display screen 59 can provide a single or multi-dimensional echocardiograph or a non-imaging A-mode display. A control console (not shown) may be provided to allow selection by the physician of the desired display format.

Alternatively, the ultrasonic transducer crystal 52 can be operated in conventional fashion without rotation, as shown in U.S. Pat. Nos. 4,697,595, or 4,706,681, or 5,358,148. Each of these patents is incorporated herein by reference.

(ii) Fiber Optic Imaging

In another embodiment (see FIG. 7), the IAE 50 comprises a fiber optic assembly 62, which permits direct visualization of tissue. Various types of fiber optic assemblies 62 can be used.

The illustrated embodiment employs a fiber optic assembly 62 of the type shown in U.S. Pat. No. 4,976,710, which is incorporated herein by reference. The assembly 62 includes a transparent balloon 64 carried at the end of the body 36. In use, the balloon 64 is inflated with a transparent gas or liquid, thereby providing a viewing window that shields the fiber optic channels 66 and 68 from blood contact.

The channels includes an incoming optical fiber channel 66, which passes through the body 36. The channel 66 is coupled to an exterior source 70 of light. The channel 66 conveys lights from the source 70 to illuminate the tissue region around the balloon 64.

The channels also include an outgoing optical fiber channel 68, which also passes through the body 36. The channel 68 is coupled to an eye piece 72, which can be carried, for example, on the handle 46. Using the eye piece 72, the physician can directly view the illuminated region.

(iii) Other Imaging

The IAE 50 can incorporate other image acquisition techniques. For example, the IAE 50 can comprise an apparatus for obtaining an image through optical coherence tomography (OCT). Image acquisition using OCT is described in Huang et al., "Optical Coherence Tomography, "*Science,* 254, Nov. 22, 1991, pp 1178–1181. A type of OCT imaging device, called an optical coherence domain reflectometer (OCDR) is disclosed in Swanson U.S. Pat. No. 5,321,501, which is incorporated herein by reference. The OCDR is capable of electronically performing two- and three-dimensional image scans over an extended longitudinal or depth range with sharp focus and high resolution and sensitivity over the range.

Figure 25:
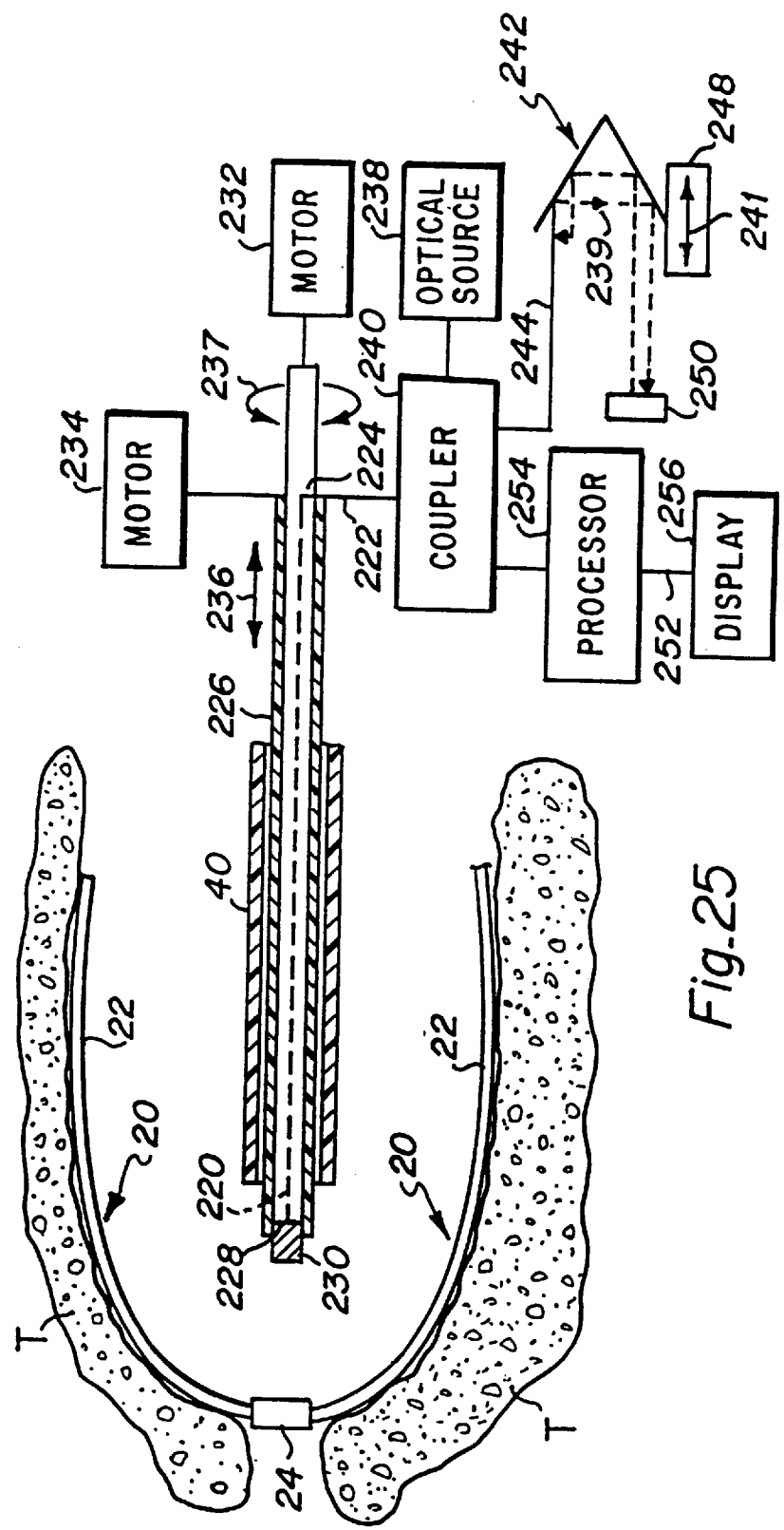
FIG. 25 is a side section view, somewhat diagrammatic in form, of a support structure that carries within it an image acquisition element comprising an optical coherence domain reflectometer.

As shown in FIG. 25, the IAE 50 comprises the distal end 220 of an optic fiber path 222. The distal end 220 is embedded within an inner sheath 224, which is carried within an outer sheath 226. The outer sheath 226 extends in the distal body region 40, within the support structure 20.

The inner sheath 224 includes a lens 228, to which the distal fiber path end 220 is optically coupled. The inner sheath 224 terminates in an angled mirror surface 230, which extends beyond the end of the outer sheath 226. The surface 230 reflects optical energy along a path that is generally perpendicular to the axis of the distal end 220.

A motor 232 rotates the inner sheath 224 within the outer sheath 226 (arrow 237). The lens 228 and the mirror surface 230 rotate with the inner sheath 224, scanning about the axis of rotation. A second motor 234 laterally moves the outer sheath 226 (arrows 236) to scan along the axis of rotation).

A source 238 of optical energy is coupled to the optic fiber path 222 through an optical coupler 240. The source 238 generates optical energy of short coherence length, preferably less than 10 micrometers. The source 238 may, for example, be a light emitting diode, super luminescent diode, or other white light source of suitable wavelength, or a short-pulse laser.

A reference optical reflector 242 is also coupled by an optic fiber path 244 to the optical coupler 240. The optical coupler 240 splits optical energy from the source 238 through the optic fiber path 222 to the distal optic path end 220 and through the optic fiber path 244 to the optical reflector 242.

The optical energy supplied to the distal optic path end 220 is transmitted by the lens 228 for reflection by the surface 230 toward tissue T. The scanned tissue T (including anatomic structures, other internal tissue topographic features, and deposits or lesions on the tissue) reflects the optic energy, as will the surrounding support structure 20.

The reflected optic energy returns via the optic path 222 to the optical coupler 240.

The optical energy supplied to the reference optical reflector 242 is reflected back to the optical coupler 240 by a corner-cube retro-reflector 246 and an end mirror 250 (as phantom lines 239 depict). The corner-cube retro-reflector 246 is mounted on a mechanism 248, which reciprocates the corner-cube retro-reflector 246 toward and away from the optical path 244 and an end mirror 250 (as arrows 241 depict). The mechanism 248 preferable moves the corner-cube retro-reflector 246 at a uniform, relatively high velocity (for example, greater than 1 cm/sec), causing Doppler shift modulation used to perform heterodyne detection.

The length or extent of movement of the corner-cube retro-reflector 246 caused by the mechanism 248 is at least slightly greater than half the scanning depth desired. The total length of the optical path 222 between the optical coupler 240 up to the desired scanning depth point is also substantially equal to the total length of the optical path 244 between the optical coupler 240 and the end mirror 250. Movement of the corner-cube retro-reflector 246 will cause periodic differences in the reflected path lengths 222 and 244.

Reflections received from the optical path 222 (from the lens 228) and the optical path 244 (from the end mirror 250) are received by the optical coupler 240. The optical coupler 240 combines the reflected optical signals. Due to movement of the corner-cube retro-reflector 246, the combined signals have interference fringes for reflections in which the difference in the reflected path lengths is less than the source coherence length. Due to movement of the corner-cube retro-reflector 246, the combined signals also have an instantaneous modulating frequency.

The combined output is coupled via fiber optic path 252 to a signal processor 254. The signal processor 254 converts the optical output of the coupler 240 to voltage-varying electrical signals, which are demodulated and analyzed by a microprocessor to provide an image output to a display device 256.

Further details of image acquisition and processing using OCDR are not essential to an understanding of the invention, but can be found in the above-cited Swanson U.S. Pat. No. 5,321,501.

C. Manipulating the Imaging Probe

Regardless of the particular construction of the IAE 50, the support structure 20 positioned about the distal region of the probe 34 remains substantially in contact against surrounding tissue mass T as the IAE 50 operates to acquire the desired image or profile (see FIGS. 5 to 8). The support structure 20 serves to stabilize the IAE 50 and keep tissue T from contacting and possible occluding the IAE 50.

Stabilizing the IAE 50 is particularly helpful when the geometry of surrounding body chamber or passage 100 is dynamically changing, such as the interior of a heart chamber during systole and diastole. The IAE 50 is thereby allowed to visualize tissue and anatomic structures T, without the attendant need for constant positioning and repositioning. The structure 20 thus makes possible the generation of accurate images of the targeted body region by the IAE 50.

(i) Manual

In a preferred embodiment (see FIG. 5A), the physician can move the IAE 50 within the structure 20 forward and rearward (respectively, arrows 101 and 103 in FIG. 5A) by pushing or pulling upon the auxiliary handle 46. By torquing the handle 46 (arrows 105 in FIG. 5A), the physician may also manually rotate the IAE 50 within the structure 20.

The illustrated and preferred embodiment further includes a mechanism 74 for deflecting, or steering, the distal region 40 of the body 36, and with it the IAE 50, transverse of the axis 89 (as depicted in phantom lines 40 in FIG. 5A).

The construction of the steering mechanism 74 can vary. In the illustrated embodiment, the steering mechanism 74 is of the type shown in U.S. Pat. No. 5,336,182, which is incorporated by reference. The steering mechanism 74 of this construction includes an actuator 76 in the auxiliary handle 46. In the illustrated embodiment, the actuator 76 takes the form of a cam wheel rotated by means of an external steering lever 78. The cam wheel 76 holds the proximal ends of right and left steering wires 80. The steering wires 80 extend from the cam wheel 76 and through the body 36. The steering wires 80 connect to the left and right sides of a resilient bendable wire 82 or spring present within the distal region 40. Rotation of the cam wheel 76 places tension on steering wires 80 to deflect the distal region 40 of the body 36, and, with it, the IAE 50 (as shown by arrows 107 in FIG. 5A).

Thus, the physician can manually move the IAE 50 with respect to the structure 20 in three principal directions. First, the IAE 50 can be moved along the axis 86 of the structure 20 by pushing and pulling on the auxiliary handle 46 (arrows 101 and 103). Second, the IAE 50 can be moved rotationally about the axis 86 of the structure 20 by torquing the auxiliary handle 46 (arrows 105). Third, the IAE 50 can be moved in a direction normal to the axis 86 of the structure 20 by operating the steering mechanism 74 (arrows 107).

By coordinating push-pull and torquing movement of the handle 46 with operation of the steering lever 78, the physician can manually move the IAE 50 in virtually any direction and along any path within the structure 20. The IAE 50 can thereby image tissue locations either in contact with the exterior surface of the structure 20 or laying outside the reach of the structure 20 itself.

(ii) Automated (Acquiring Image Slices)

FIG. 9 shows an electromechanical system 102 for manipulating the IAE 50 within the structure 20. The system 102 synchronizes the imaging rate of the IAE 50 with movement of the IAE 50 within the structure 20. The system allows the physician to use the structure 20 to accurately acquire a set of image slices, which can be processed in an automated fashion for display.

The details of the system 102 can vary. As shown in FIG. 9, the system 102 includes a longitudinal position translator 104 mechanically coupled to the probe handle 46. The translator 104 includes a stepper motor 106 that incrementally moves an axial screw 111 attached to the handle 46. The motor 106 rotates the screw 111 to move the IAE 50 at a specified axial translation rate within the structure 20, either forward (arrows 101) or rearward (arrows 103). As FIG. 9 shows, during axial translation, the distal body region 40 carrying the IAE 50 is preferably maintained in a generally straight configuration, without transverse deflection. By synchronizing the axial translation of the IAE 50 within the structure 20 with the imaging rate of the IAE 50, the system 102 provides as output axially spaced, data sample slices of the region surrounding the IAE 50.

For example, the use of an axial translator 104 of the general type shown in FIG. 4 in combination with a rotating transducer crystal 52 of the type shown in FIG. 6 is described in U.S. Pat. No. 5,485,846, which is incorporated herein by reference. By rotating the transducer crystal 52 in synchrony with the axial translation rate of the translator 104, the system 102 provides axially spaced, 360° data sample slices of the region perpendicular to the transducer crystal 52. Conventional signal processing techniques are used to reconstruct the data slices taken at specified intervals along the axis into three-dimensional images for display. This technique is well suited for acquiring images inside blood vessels or other body regions having a known, relatively stable geometry.

When used to acquire images inside a beating heart chamber, the stepper motor 106 is preferable gated by a gating circuit 190 (see FIG. 9) to the QRS of an electrocardiogram taken simultaneously with image gathering, for example, by using a surface electrode 188 shown in FIG. 9. The gating circuit 190 is also synchronized with the imaging system 54 (as described in greater detail in conjunction with FIG. 6), so that the data image slices are recorded in axial increments at either end-diastolic or end-systolic points of the heart beat. When imaging an atrium, the data slice recordings are preferably gated to the p-wave. When imaging a ventricle, the imaging is preferably gated to the r-wave.

Alternatively, the circuit 190 is gated to the timing of local intracardiac electrogram activation. In this arrangement (see FIG. 21), the flexible body 36, which carries the transducer 54 within the structure 20, also carries an electrode 184 to sense electrograms in the region of the structure 20. The sensed electrograms are conveyed to the circuit 190 to gate the stepper motor 106, as before described. When imaging an atrium, the data slice recordings are gated to the atrial intracardiac electrogram activation. Likewise, when imaging a ventricle, the data slice recordings are gated to the ventricular intracardiac electrogram activation.

As FIG. 21 shows, the body 36 carrying the transducer 54 and the electrode 184 is preferably confined for movement within a straight, generally rigid sheath 186. The sheath 186 guides the body 36 along a known, stable reference axis 183.

The sheath 186 is also preferably constructed of an ultrasonically transparent material, like polyethylene. The transducer 54 and electrode 184 move in tandem within the confines of the sheath 186 (as shown by arrows 187 and 189 in FIG. 21) in response to the gated action of the stepper motor 106. Because the sheath 186 is ultrasonically transparent, the transducer 54 can remain within the confines of the sheath 186 while acquiring images. Nonlinearities in image reconstruction caused by deflection of the transducer outside of the axis 183, as would occur should the transducer 54 move beyond the sheath 186, are avoided. The acquired data image slices, position-gated by the electrograms while maintained along a known, stable reference axis 183, are generated for accurate reconstruction into the desired three-dimensional image.

Alternatively, a catheter tracking system as described in Smith et al. U.S. Pat. No. 5,515,853 may be used to track the location and orientation of the IAE 50 during movement. Another system that can be used for this purpose is disclosed in copending U.S. patent application Ser. No. 08/717,153, filed Sep. 20, 1996 and entitled "Enhanced Accuracy of 3-Dimensional Intraluminal Ultrasound (ILUS) Image Reconstruction," naming Harm TenHoff as an inventor.

(iii) Localized Guidance

The structure 20 itself can establish a localized position-coordinate matrix about the IAE 50. The matrix makes it possible to ascertain and thereby guide the relative position of the IAE 50 within the structure 20 (and thus within the targeted body cavity), to image specific regions within the targeted body cavity.

In this embodiment (see FIG. 10), the IAE 50 carries an electrode 31 for transmitting electrical energy. Likewise, each spline 22 carries an array of multiple electrodes 30 for transmitting electrical energy.

In the illustrated embodiment (see FIG. 11), the electrodes 30 are supported about the core body 84 on the flexible, electrically nonconductive sleeve 32, already described. The electrodes 30 are electrically coupled by wires (not shown), which extend beneath the sleeve 32 through the catheter tube 12 to external connectors 32, which the handle 18 carries (see FIG. 1).

In the illustrated embodiment, each electrode 30 comprises a solid ring of conductive material, like platinum, which is pressure fitted about the sleeve 32. Alternatively, the electrodes 30 comprise a conductive material, like platinum-iridium or gold, coated upon the sleeve 32 using conventional coating techniques or an ion beam assisted deposition (IBAD) process. Still alternatively, the electrodes 30 comprise spaced apart lengths of closely wound, spiral coils wrapped about the sleeve 32. The coils are made of electrically conducting material, like copper alloy, platinum, or stainless steel. The electrically conducting material of the coils can be further coated with platinum-iridium or gold to improve its conduction properties and biocompatibility. Further details of the use of coiled electrodes are found in U.S. Pat. No. 5,545,193 entitled "Helically Wound Radio-Frequency Emitting Electrodes for Creating Lesions in Body Tissue," which is incorporated herein by reference.

In yet another alternative embodiment, the electrodes 30 can be formed as part of a ribbon cable circuit assembly, as shown in pending U.S. application Ser. No. 08/206,414, filed Mar. 4, 1994, which is incorporated herein by reference.

In this arrangement (see FIG. 10), a micro-processor controlled guidance element 108 is electrically coupled to the electrodes 30 on the structure 20 and the electrode 31 carried by the IAE 50. The element 108 conditions the electrodes 30 on the structure 20 and the IAE electrode 31 to generate an electric field (shown in phantom lines 113 in FIG. 10) within the structure 20, while also sensing electrode electric potentials in the electric field. More particularly, the element 108 commands a transmitting electrode, which can be either the IAE electrode 31 or at least one of the electrodes 30 in the structure 20, to transmit electrical energy. The element 108 commands a sensing electrode, which also can be either the IAE electrode 31 or at least one of the electrodes 30 on the structure 20, to sense electrical energy emitted by the emitting electrode.

The element 108 generates an output by analyzing spatial variations in the electrical potentials within the field 113, which change based upon the relative position of the IAE electrode 31 relative to electrode 30 on the structure 20. The variations can comprise variations in phase, variations in amplitude, or both. Alternatively, the element 108 generates an output by analyzing spatial variations in impedances between the transmitting and sensing electrodes. The output locates the IAE 50 within the space defined by the structure 20, in terms of its position relative to the position of the multiple electrodes 30 on the structure 20.

The element 108 includes an output display device 110 (e.g., a CRT, LED display, or a printer), which presents the position-identifying output in a real-time format most useful to the physician for remotely guiding the IAE 50 within the structure 20.

Further details of establishing a localized coordinate matrix within a multiple electrode structure for the purpose of locating and guiding the movable electrode within the structure are found in copending U.S. patent application Ser. No. 08/320,301, filed Oct. 11, 1994 and entitled "Systems and Methods for Guiding Movable Electrode Elements Within Multiple Electrode Structures." This application is incorporated herein by reference.

Figure 26:
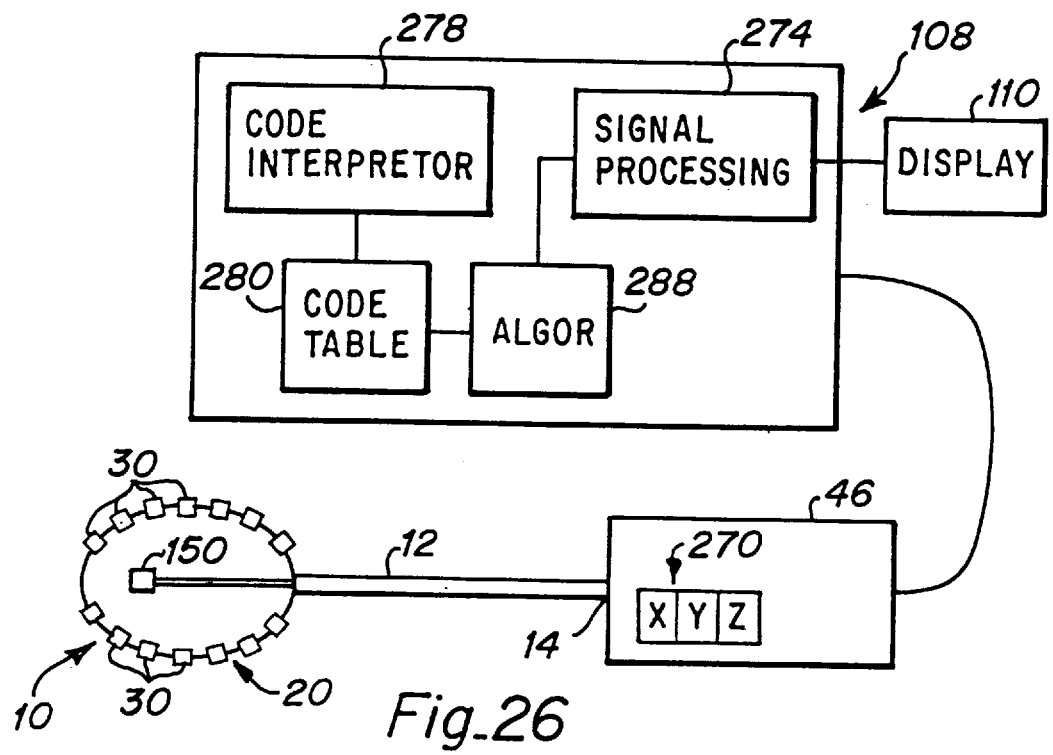
FIG. 26 is a diagrammatic view of a system for identifying the physical characteristics of a support structure using a machine-readable code, to enable the creation of a positioning matrix (shown in FIG. 10) to guide the imaging probe within the structure.

In a preferred embodiment (see FIG. 26), structure 20 carries an identification component 270. The identification component 270 carries an assigned identification code XYZ. The code XYZ identifies the shape and size of the structure 20 and the distribution of electrodes 30 carried by the structure 20, in terms of the number of electrodes and their spatial arrangement on the structure 20. The structure-specific information contained in the code XYZ aids the element 108 in creating a positioning matrix using the electrodes 30, to help guide the IAE 50 within the structure 20.

In the illustrated embodiment (see FIG. 26), the coded component 270 is located within the handle 46 attached to the proximal end 14 of the catheter tube 12 that carries the structure 20. However, the component 270 could be located elsewhere in relation the structure 20.

The coded component 270 is electrically coupled to an external interpreter 278 when the structure 20 is coupled to the element 108 for use. The interpreter 278 inputs the code XYZ that the coded component 270 contains. The interpreter 278 electronically compares the input code XYZ to, for example, a preestablished master table 280 of codes contained in memory. The master table 280 lists, for each code XYZ, the structure-specific information required to create the positioning matrix to guide the IAE 50 within the structure 20.

The element 108 preferably includes functional algorithms 288 which set guidance parameters based upon the code XYZ. These guidance parameters are used by the signal processing component 274 of the element in analyzing the spatial variations of the electric field created within the structure 20 to guide the IAE 150. The guidance parameters are also used to create the position-identifying output displayed on the device 110.

Because knowledge of the physical characteristic of the structure 20 and the spatial relationship of the electrodes 30 is important in setting accurate guidance parameters, the algorithms 288 preferably disable the guidance signal processing component 274 in the absence of a recognizable code XYX. Thus, only structures 20 possessing a coded component 270 carrying the appropriate identification code XYZ can be used in association with the element 108 to guide the IAE 50.

Figure 27:
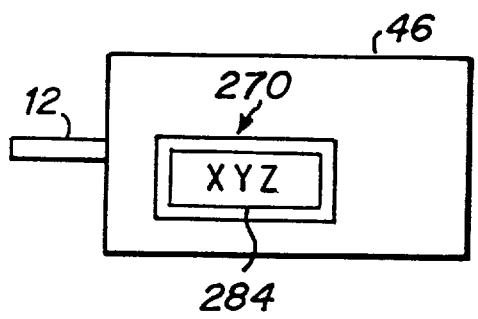
FIG. 27 is a diagrammatic view of one implementation of the machine-readable code used to identify the individual physical characteristics of the support structure shown in FIG. 26.

The coded component 270 can be variously constructed. It can, for example, take the form of an integrated circuit 284 (see FIG. 27), which expresses in digital form the code XYZ for input in ROM chips, EPROM chips, RAM chips, resistors, capacitors, programmed logic devices (PLD's), or diodes. Examples of catheter identification techniques of this type are shown in Jackson et al. U.S. Pat. No. 5,383,874, which is incorporated herein by reference.

Figure 28:
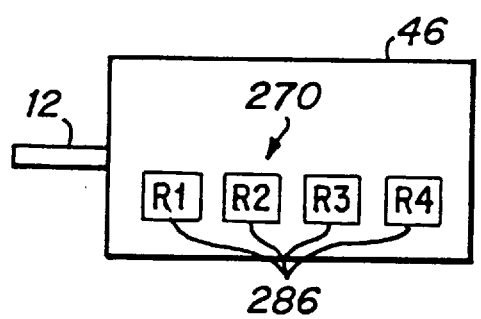
FIG. 28 is a diagrammatic view of another implementation of the machine-readable code used to identify the individual physical characteristics of the support structure shown in FIG. 26.

Alternatively, the coded component 270 can comprise separate electrical elements 286 (see FIG. 28), each one of which expressing a individual characteristic. For example, the electrical elements 286 can comprise resistors (R1 to R4), comprising different resistance values, coupled in parallel. The interpreter 278 measures the resistance value of each resistor R1 to R4. The resistance value of the first resistor R1 expresses in preestablished code, for example, the number of electrodes on the structure. The resistance value of the second resistor R2 expresses in preestablished code, for example, the distribution of electrodes on the structure. The resistance value of the third resistor R3 expresses in preestablished code, for example, the size of the structure. The resistance value of the fourth resistor R4 expresses in preestablished code, for example, the shape of the structure.

Alternatively, the electrodes 30/31 can define passive markers that, in use, do not transmit or sense electrical energy. The markers are detected by the physician using, for example, external fluoroscopy, magnetic imaging, or x-ray to establish the location of the structure 20 and the IAE 50.

D. Multiple Phased Transducer Arrays

The stability and support that the structure 20 provides the IAE 50 is well suited for use in association with an IAE 50 having one or more phased array transducer assemblies. The stability and support provided by the structure 20 make it possible to accommodate diverse numbers and locations of phased array transducers in close proximity to tissue, to further enhance the resolution and accuracy of images created by the IAE 50.

In one embodiment, as FIG. 22 shows, the structure 20 carries an IAE 50 comprising a phased array 192 of ultrasonic transducers of the type shown, for example, in Shaulov U.S. Pat. 4,671,293, which is incorporated herein by reference. As FIG. 22 shows, the array 192 includes two groups 194 and 196 of electrodes. The electrode groups 194 and 196 are differently partitioned by channels 206 on opposite faces or planar sectors 194' and 196' of a piezoelectric material 198. The channels 206 cut through the electrode surfaces partially into and through the piezoelectric material 198 to prevent mechanical and electrical coupling of the elements.

The channels 206 on the planar section 194' create spaced transducer elements 202a, 202b, 202c, etc. Likewise, the channels 206 on the planar section 196' create spaced transducer elements 204a, 204b, 204c, etc.

The electrode groups 194 and 196 are alternatively pulsed by a conventional phase array circuit 200. During one pulse cycle, the electrode element group 194 is grounded, while the transducer elements 204a, 204b, 204c, etc. on the other planar section 196' are simultaneously pulsed, with the phase relationship of the stimulation among the transducer elements 204a, 204b, 204c, etc. set to create a desired beam angle, acquiring an image along the one planar sector 196'. During the next pulse cycle, the other electrode element group 196 is grounded, while the transducer elements 202a, 202b, 202c, etc. on the other planar section 194' are likewise simultaneously pulsed, acquiring another image along the planar sector 194'. Further details, not essential to the invention, are provided in Haykin, *Adaptive Filter Theory*, Prentice-Hall, Inc. (1991), pp. 60 to 65.

The signals received by the transducer groups 202a, 202b, 202c, etc. and 204a, 204b, 204c, etc., when pulsed, are processed into amplitude, phase, frequency, and time response components. The processed signals are compared to known configurations with varying transducers activated to produce and measure the desired waveform. When signals from combinations of transducers are processed, a composite image is produced.

The phased array 192 shown in FIG. 22 permits the real time imaging of two different planar sectors, which can be at any angle with respect to each other.

Figure 23:
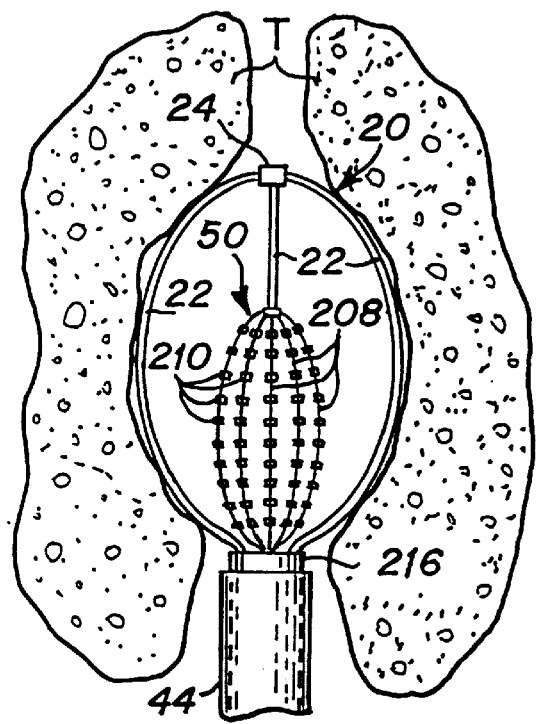
FIG. 23 is a side section view of a support structure that carries within it an image acquisition element comprising a phased multiple transducer array carried on flexible spline elements.
Figure 24:
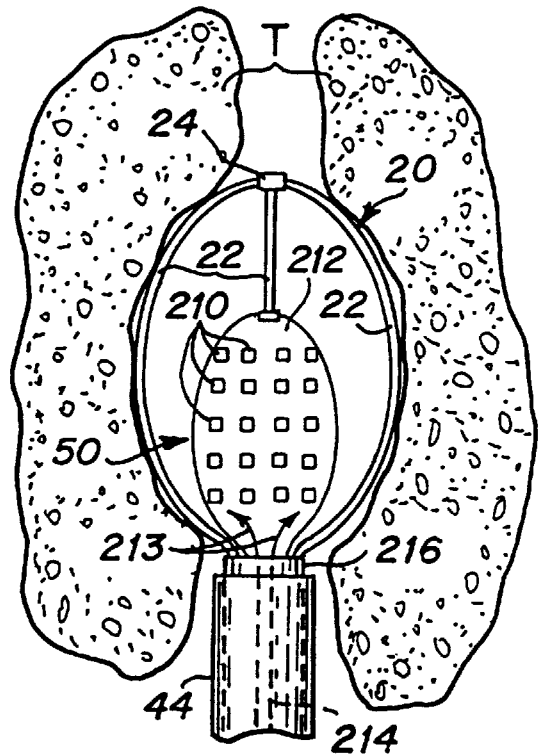
FIG. 24 is a side section view of a support structure that carries within it an image acquisition element comprising a phased multiple transducer array carried on an expandable-collapsible body.

FIGS. 23 and 24 show other embodiments of an IAE 50 comprising a phased array of transducers carried within the structure 20.

In the embodiment shown in FIG. 23, the IAE 50 comprises an array of flexible spline elements 208 having a known geometry. The spline elements 208 are carried within the support structure 20, which itself comprises a larger diameter array of flexible spline elements 22, as previously discussed in conjunction with FIG. 1. Each flexible spline element 208 carries a grouping of multiple ultrasonic transducers 210.

Collapsing the outer structure 20 of spline elements 22 by advancing the sheath 44 (previously described and shown in FIGS. 1 and 2) also collapses the inner IAE structure of spline elements 208. The mutually collapsed geometry presents a low profile allowing joint introduction of the structures 22 and 208 into the desired body region.

In the embodiment shown in FIG. 24, the IAE 50 comprises an expandable-collapsible body 212 carried within the support structure 20. Again, the structure 20 is shown as comprising the array of flexible spline elements 22. Like the flexible spline elements 208 shown in FIG. 23, the exterior surface of the body 212 carries an array of multiple ultrasonic transducers 210.

An interior lumen 214 within the body 216 carrying the IAE 50 conducts a fluid under pressure into the interior of the body 212 (as shown by arrows 213 in FIG. 24) to inflate it into a known expanded geometry for use. In the absence of the fluid, the body 212 assumes a collapsed geometry (not shown). The advanced sheath 44 envelopes the collapsed body 212, along with the outer structure 20, for introduction into the desired body region.

In the illustrated embodiment, the ultrasonic transducers 210 are placed upon the spline elements 208 or expandable body 212 (which will be collectively called the "substrate") by depositing desired transducer materials or composites thereof onto the substrate. Ion beam assisted deposition, vapor deposition, sputtering, or other methods can be used for this purpose.

To create a spaced apart array of transducers 210, a masking material is placed on the substrate to keep regions free of the deposited material. Removal of the masking material after deposition of the transducer materials provides the spaced apart array on the substrate. Alternatively, an etching process may be used to selectively remove sectors of the transducer material from the substrate to form the desired spaced apart array. The size of each deposited transducer 210 and the density of the overall array of transducers 210 should be balanced against the flexibility desired for the substrate, as conventional transducer material tends to be inherently stiffer than the underlying substrate.

Alternatively, transducers 210 can be attached in a preformed state by adhesives or the like to the spline elements 208 or flexible body 212. Again, the size of each attached transducer 210 and the density of the overall array of transducers 210 should be balanced against the flexibility desired for the substrate.

Signal wires may be coupled to the transducers 210 in various ways after or during deposition or attachment; for example by soldering, or by adhesive, or by being deposited over. Various other ways to couple signal wires to solid or deposited surfaces on an expandable-collapsible body are discussed in copending patent application Ser. No. 08/629,363, entitled "Enhanced Electrical Connections for Electrode Structures," filed Apr. 8, 1996, which is incorporated herein by reference.

The signal wires may be bundled together for passage through the associated catheter tube 12, or housed in ribbon cables for the same purpose in the manner disclosed in Kordis U.S. Pat. No. 5,499,981, which is incorporated herein by reference.

It should be appreciated that the multiple ultrasonic transducers 210 could be supported on other types of bodies within the structure 20. For example, non-collapsible hemispherical or cylindrical bodies, having fixed predetermined geometries, could occupy the interior of the structure 20 for the purpose of supporting phased arrays of ultrasonic transducers 210. Alternatively, the signal wires and transducers may be braided into a desired three-dimensional structure. The braided structure may further be laminated to produce an inflatable balloon-like structure. The dimensions of these alternative transducer support bodies can vary, subject to the requirement of accommodating introduction and deployment in an interior body region.

Other examples of phased arrays of multiple transducers are found, for example, in Griffith et al. U.S. Pat. No. 4,841,977 and Proudian et al. U.S. Pat. No. 4,917,097.

Phased arrays of multiple transducers may be used in association with gating techniques, described above in conjunction with FIG. 9, to lessen the image acquisition time. In the dynamic environment of the heart, gating may be used to synchronize the phased acquisition of multiple plane images with the QRS or intracardiac electrogram activation, particularly if it is desired to analyze the images over more than one heart beat.

E. Visualization During Cardiac Mapping Procedures

(i) Electrical Activity Sensing

As just shown (see FIG. 10) and described, the structure 20 can carry an array of electrodes 30 for the purpose of guiding the IAE 50. These same electrodes 30 can also serve to sense electrical impulses in tissue, like myocardial tissue. This sensing function in heart tissue is commonly called "mapping."

As FIG. 10 shows, when deployed for use inside a heart chamber, the support structure 20 holds the electrodes 30 in contact against the endocardium. The electrodes sense the electrical impulses within the myocardium that control heart function. In this arrangement the element 108 includes or constitutes an external signal processor made, for example, by Prucka Engineering, Inc. (Houston, Tex.). The processed signals are analyzed to locate aberrant conductive pathways and identify foci. The foci point to potential ablation sites.

Alternatively, or in combination with mapping, the electrodes 30 on the support structure 20 can be used to derive an electrical characteristic, such as impedance, in heart tissue for the purpose of characterizing tissue and locating aberrant conductive pathways. Systems and methods for deriving an electrical characteristic of tissue for this purpose are disclosed, for example, in Panescu et al U.S. Pat. No. 5,494,042, which is incorporated herein by reference. An electrical characteristic is derived by transmitting electrical energy from one or more electrodes into tissue and sensing the resulting flow of electrical energy through the tissue.

The IAE 50 carried within the multiple electrode structure 20 greatly assists the physician in mapping or characterizing tissue, whether in the heart or elsewhere in the body, by locating the electrodes 30 in the desired orientation with respect to selected anatomic sites. For example, when used within the heart, the physician can manipulate the IAE 50 in the manners previously described to visual identify the coronary sinus, heart valves, superior and inferior vena cava, the fossa ovalis, the pulmonary veins, and other key anatomic sites in the heart. Relying upon the visual information obtained by the IAE 50, the physician can then orient the multiple electrode structure 20 with respect to one or more of these anatomic sites. Once properly oriented, the physician can further visualize with the IAE 50, to assure that all or a desired number of the electrodes 30 carried by the structure 20 are in intimate contact with tissue required for good signal transmission or good signal acquisition.

As FIG. 12 shows, the IAE 50 can also be used to help visually steer a separate mapping electrode 112, carried on its own catheter tube 121, outside or within the support structure 20 into the desired location in contact with heart tissue. If the roving electrode 112 is present within the confines of the support structure 20, the structure 20 also serves to stabilize the electrode 112. The guidance processing element 108 as previously described (see FIG. 10) can be used in association with the structure 20 to electronically home the external mapping electrode 112 to a desired location within the structure 20.

(ii) Contrast Echocardiography

FIG. 8 shows a system 170 that includes the structure 20 carrying an IAE 50 to identify perfusion patterns in myocardial tissue and, thereby, diagnose potential ablation sites within the heart. In this embodiment, the IAE 50 carried within the structure 20 comprises a rotating ultrasonic transducer 52 of the type previously described in conjunction with FIG. 6. The system 170 shown in FIG. 8 also preferably includes an electro-mechanical system 102 for incrementally moving the transducer 52 within the structure 20 to obtain axially spaced, data sample slices of the region surrounding the transducer 52. The details of this the system 102 have been previously described in conjunction with FIG. 9. The electro-mechanical system 102 may also be gated to the QRS of an electrocardiogram or to intracardiac electrogram activation to acquire images at either end-diastolic or end-systolic points of the heart cycle, in the manner also previously described in conjunction with FIGS. 9 or 21.

The system 170 shown in FIG. 8 includes a separate catheter 172. The catheter 172 includes an interior lumen 174, which is coupled to a source of an echoluscient contrast media 176. The catheter 172 injects the media 176 into the blood stream.

The echoluscient contrast media 176 used may vary. In a preferred embodiment, the media 176 comprises sonicated albumin microbubbles, or their equivalent, having a diameter smaller than red blood cells (which are typically about 8 μm).

When carried within the blood stream, the microbubbles in the media 176 are perfused into tissue, just as the blood components that accompany them. The microbubbles in the media 176, perfused into tissue, strongly scatter ultrasonic waves. They appear ultrasonically "bright" in contrast to the less ultrasonically "bright" cellular components of blood also perfused into tissue. The physician is thereby able to accurately observe the patterns of perfusion of the media 176 into tissue. The more volume of media 176 perfused into tissue, the brighter the ultrasonic image, and vice versa.

Myocardial tissue that has been infarcted has significantly lower perfusion characteristics than healthy myocardial tissue. See, for example, Nath et al., "Effects of Radiofrequency Catheter Ablation on Regional Myocardial Blood Flow," *Circulation,* 1994; 89: 2667–2672; and Villaneuva et al., "Assessment of Risk Area During Coronary Occlusion and Infarct Size After Reperfusion with Myocardial Contrast Echocardiography Using Left and Right Atrial Injections of Contrast," *Circulation,* 1993; 88:596–604).

As FIG. 8 shows, the catheter 172 is preferably maneuvered percutaneously into a selected coronary vessel. The contrast media 176 is injected through the catheter lumen 174 into the vessel, and thus into the vascular system near the heart.

If the selected vessel is the coronary artery, the media 176 is distributed throughout the regions of the heart perfused by the coronary artery, increasing the resolution and contrast in a selected localized region. More global distribution of contrast media 176 can be obtained by selecting an injection site in one of the heart chambers or in the pulmonary artery.

For example, if myocardial tissue in the basil or posteriolateral aspect of the left ventricle is slated for diagnosis, the catheter 172 is preferably maneuvered to inject the media 176 into the circumflex coronary artery branch of the left main artery. If myocardial tissue in the anterior aspect of the right or left ventricles is slated for diagnosis, the catheter 172 is preferably maneuvered to inject the media 176 into the left anterior descending (LAD) coronary artery branch of the left main artery. If myocardial tissue in the free wall of the right ventricle or the posterior ventricular septum is slated for diagnosis, the catheter 172 is preferably maneuvered to inject the media 176 into the right coronary artery.

Alternatively, the media 176 can be injected directly into the left atrium or left ventricle. In this arrangement, the body 36 carrying the transducer 52 can also include an interior lumen 178 to convey the media 176. This approach may be easier and potentially less traumatic than injection directly into the coronary artery. However, a portion of the media 176 will still be dispersed past the coronary arteries and through the systemic arterial system, thereby resulting in a poorer resolution per given volume of media 176 injected. Therefore, a larger volume of media 176 should be injected directly into the left atrium or ventricle to obtain contrast in myocardial tissue comparable to a smaller volume of media 176 injected directly into a coronary artery, as described above.

Furthermore, contrast media 176 may be injected systemically into the femoral vein. Again, with this approach, significant portions of the media 176 will be disbursed within the circulatory system, and, in particular, into the lungs. As just discussed, a larger volume of media 176 should be injected systemically into the femoral vein to obtain contrast in myocardial tissue comparable to a smaller volume of media 176 injected directly into a coronary artery.

The system 170 includes a receiver and processor 180 and display device 182, as earlier described in conjunction with FIG. 6. In synchrony with the axial translation system 102, the receiver and processor 180 preferably creates a three-dimensional image for display on the device 182. Alternatively, an echocardiographic image may be created for display without using the axial translation system 102.

The contrast media 176 highlights the differences in perfusion in myocardial tissue surrounding the structure 20. Regions of infarcted tissue are visually characterized, as they are not well perfused with blood and appear in negative contrast to the healthy tissue regions that are well perfused. The same visually characterized, negative contrast regions of infarcted tissue may also form part of the pathways of slow conduction of electrical impulses. These slow conduction pathways may be a substrate for ventricular tachycardia and therefore candidates for cardiac ablation. These candidate regions of slow conduction pathways will, in the presence of the contrast media 186, appear on the ultrasonic device 182 as zones of negative contrast, being significantly less ultrasonically "bright" than well perfused tissue regions. The candidate regions of slow conduction will typically have infarcted tissue interspersed with well perfused tissue. The candidate regions will therefore appear ultrasonically "mottled", with patchy regions of darker contrast interspersed with lighter contrast. The mottled zones will appear contiguous to negative contrast areas. The image resolution of the device 182 should preferably be fine enough to discern among mottled zones, light contrast zones, and dark contrast zones.

The support structure 20 maintains the transducer 54 in a stable, substantially unobstructed viewing position near the targeted tissue region. The transducer 54 thereby generates ultrasonic images of the differences in perfusion of the media 176 throughout the imaged heart tissue. The system 170 therefore make possible the accurate characterization of tissue for identifying potential ablation sites using contrast echocardiography.

In addition to identifying candidate ablation sites, the stable, unobstructed perfusion images that the system 170 provides, also make it possible to discern the lesion characteristic required to treat the arrhythmia. The perfusion pattern may indicate a localized, contained mottled contrast area, suited for treatment by creating an equally localized, small surface area lesion. Alternatively, the perfusion pattern may indicate a larger or deeper mottled contrast area, or a mottled contrast area that is elongated or a random complex of different, intersecting geometries. These instances give rise to the need for corresponding larger or deeper lesion patterns, or long or intersecting legion patterns, or lesion patterns otherwise having geometries tailored to the geometry of the mottled contrast area.

The stable, unobstructed perfusion images that the system 170 provides also make it possible to characterize tissue substrates associated with polymorphic ventricular tachycardia. The system 170 makes it possible to characterized these regions using echocardiography during normal sinus rhythm. Conventional mapping of electrical events requires induction of sometimes hemodynamically unstable rhythms to locate and ablate substrates associated with polymorphic ventricular tachycardia.

The stable, unobstructed perfusion images that the system 170 provides also make it possible to discern intermediate contrast zones between "bright" (well perfused tissue) images and negative contrast (not well perfused, infarcted tissue) images. These intermediate contrast zones also delineate the infarcted tissue border. Once identified, tissue ablation can be conducted with the objective of ablating tissue within the border zone, to eliminate the potential for ventricular tachycardia substrates.

The system 170 may characterize tissue morphology based upon echocardiography to locate potential ablation sites in other ways. For example, the system 170 may image based upon ultrasonic frequency domain analyses. For example, the intensity of the second harmonics can be used to identify tissue morphologies such as scar tissue, ischemic tissue, infarcted tissue, and healthy tissue as a function of tissue elasticity. Frequency domain analyses like second harmonics may be used without the injection of contrast media 170 to characterize tissue for ablation purposes.

The system 170 for carrying out contrast echocardiography may also incorporate an IAE 50 comprising multiple transducers and using phased array techniques to enhance the perfusion images, as previously described in conjunction with FIGS. 22 to 24.

FIG. 8 shows the system 170 being used in association with intracardiac echocardiography. It should also be appreciated that the echocardiography can be used to characterize tissue morphology, and thereby identify potential ablation sites, using external ultrasound transducers located outside the body.

It should also be appreciated that the system 170 can be used as an adjunct to other echography procedures; for example, transesophageal or transthoracic echography.

The analysis of tissue perfusion patterns to characterize myocardial tissue to locate potential ablation sites can also be accomplished using external imaging techniques other than echography. For example, magnetic resonance imaging (MRI) can be used. Using MRI, an isotope, such as gadolinium-chelate, is injected to serve as the contrast material. As another example, computerized tomography (CT) scanning can be used. Using CT, iodine radiopaque compounds, such as renografin, can be injected to serve as the contrast material. As another example, nuclear imaging using thallium as the contrast material can be used. Using any of these alternative imaging techniques, slow conduction pathways in myocardial tissue will, in the presence of the appropriate contrast media, appear as zones of negative or mottled contrast. As before discussed, the image resolution of the alternative technique should preferably be fine enough to discern among mottled zones, light contrast zones, and dark contrast zones. The alternative imaging techniques, like echography, can also be used to discern intermediate contrast zones, which delineate infarcted tissue borders.

II. Visualization for Therapeutic Purposes

The foregoing description of the structure 20 and associated IAE 50 exemplify use in the performance of general diagnostic functions, to accurately locate and identify abnormalities that may be present in body cavities or in electrical activities within tissue. The structure 20 and associated IAE 50 can also aid in providing therapeutic functions, alone or in combination with these and other diagnostic functions.

The following exemplifies this use in the context of treating cardiac arrhythmias. However, it will be appreciated that there are diverse applications where the invention can serve therapeutic functions or both diagnostic and therapeutic functions.

A. Lesion Formation

Once a potential ablation site has been identified by mapping (typically, in the ventricle), or by reference to an anatomic landmark within the heart (typically, in the atrium), or by deriving an electrical characteristic, the physician deploys an ablation element to the site. While various types of ablation energy can be used, in the preferred implementation, the ablation electrode transmits radio frequency energy conveyed from an external generator (not shown). The ablation element can takes various forms, depending upon the type of lesion required, which, in turn, depends upon the therapeutic effect desired.

(i) Smaller Lesions

Typically, lesions that are characterized as "small and shallow" have a depth of about 0.5 cm, a width of about 10 mm, and a lesion volume of up to 0.2 cm$^3$. FIG. 16 exemplifies the geometry for a typical "small" lesion 118. These lesions are desired in the sinus node for sinus node modifications, or along the A-V groove for various accessory pathway ablations, or along the slow zone of the tricuspid isthmus for atrial flutter (AFL) or AV node slow pathways ablations. For this purpose, a physician will typically deploy an electrode having approximately an 8 F diameter and a 4 mm length to transmit radio frequency energy to create small and shallow lesions in myocardial tissue.

This type of ablation electrode can be used in association with the support structure 20, even when the catheter tube bore is occupied by the imaging probe 34. In this arrangement (see FIG. 12), the physician separately deploys the ablation electrode as a "roving" electrode 112 outside the support structure 20. The physician then steers the external electrode 112 into the confines of the support structure 20 for ablation (such an electrode 112 can also perform an auxiliary mapping function, as already described). Usually, the electrode 112 is preferably operated in a uni-polar mode during ablation, in which the radio frequency ablation energy transmitted by the electrode 112 is returned through an indifferent patch electrode 114 externally attached to the skin of the patient.

The support structure 20 serves to stabilize the external "roving" ablation electrode 112 within a confined region of the heart. The IAE 50 can be used in this arrangement to help visually navigate the roving ablation electrode 112 into the desired location in contact with heart tissue. The guidance processing element 108 as previously described (see FIG. 10) can also be used in association with the structure 20 to electronically home the roving ablation electrode 112 to the desired ablation site contacting the support structure 20.

Alternatively (as FIGS. 5 and 10 show), the electrode 31 that the IAE 50 carries can comprise an ablation electrode, in the manner shown in U.S. Pat. No. 5,385,148, which is incorporated herein by reference. The exterior diameter of the IAE 50 (with electrode 31) is preferably larger than the interior diameter of the catheter tube bore 38 (see FIG. 5A). Thus, while the IAE 50 (and electrode 31) can be freely moved within the structure 20 in the manner already described, it cannot be withdrawn into the catheter tube bore.

In this arrangement, the slidable sheath 44 that encloses the structure 20 during deployment (see FIG. 2), also encloses the IAE 50 and ablation element 31 within the collapsed structure 20. Further details of a structure integrating a movable element within a multiple electrode support structure can be found in U.S. Pat. No. 5,476,495, which is incorporated herein by reference.

As before explained, the guidance processing element 108 (FIG. 10) can also create a position-identifying output in a real-time format most useful to the physician for guiding the ablation electrode 31 carried by the IAE 50 within the structure 20 toward a potential site identified for ablation.

In an alternative embodiment, the exterior diameter of the IAE 50 (with electrode 31) is smaller than the interior diameter of the catheter tube bore 38. The IAE 50 and the entire imaging probe 34 can thereby be withdrawn through the catheter tube bore 38 from the catheter tube 12. In this arrangement, the catheter tube 12 carrying the multiple electrode support structure 20 and the imaging probe 34 comprise separately deployed components. The imaging probe 34 is deployed through the catheter tube 12 only when the visualization function is required. When the imaging probe 34 is withdrawn, the catheter tube bore 38 is open to provide passage for other components; for example, the separate mapping or ablation electrode 112 shown in FIG. 12. In this arrangement, the imaging probe 34 can be switched in situ with the mapping or ablation electrode 112, without altering the position of the structure 20.

(ii) Larger Lesions

The elimination of ventricular tachycardia (VT) substrates is thought to require significantly larger and deeper lesions, with a penetration depth greater than 1.5 cm, a width of more than 2.0 cm, with a lesion volume of at least 1 cm$^3$. There also remains the need to create lesions having relatively large surface areas with shallow depths. FIG. 17 exemplifies the geometry of a typical larger surface area lesion 120, compared to the geometry of the smaller lesion 118 shown in FIG. 16.

FIGS. 13A and 13B show an alternative embodiment of the invention, which provides a composite structure 122 carrying an imaging probe 124 and an ablation element 126, which is capable of providing larger lesions. The composite structure 122 (like structure 20 shown in FIG. 1) is carried at the distal end of a flexible catheter tube 12. The proximal end of the catheter tube carries an attached handle 18 for manipulating the composite structure in the manners previously described.

The composite structure 122 comprises an expandable-collapsible hollow body 128 made from a porous transparent thermoplastic or elastomeric material. The size of the pores 129 in the body 128 are exaggerated for the purpose of illustration in FIG. 13A. The entire body 128 may be porous, or the body 128 may include a discrete porous region.

The body 128 carries within it an interior electrode 130, which is formed of an electrically conductive material that has both a relatively high electrical conductivity and a relatively high thermal conductivity. Materials possessing these characteristics include gold, platinum, platinum/iridium, among others. Noble metals are preferred. An insulated signal wire 132 is coupled to the electrode 130, which electrically couples the electrode 130 to an external radio frequency generator 134.

An interior lumen 136 within the catheter tube 12 conducts an electrically conductive liquid 140 under pressure from an external source 138 into the hollow interior of the expandable-collapsible body 128. As FIG. 13A shows, the electrically conductive liquid 140 inflates the body 128 to an enlarged, or expanded, geometry. As will be explained later, it is this expanded geometry that makes possible the formation of the larger lesions desired. As FIG. 13B shows, in the absence of the fluid 140, the expandable-collapsible body 128 assumes a collapsed, low profile. It is this low profile that permits straightforward introduction of the structure 122 into the body.

When radio frequency energy is transmitted by the interior electrode 130, the electrically conductive liquid 140 within the body 128 establishes an electrically conductive path. The pores of the porous body 128 establish ionic transport of ablation energy from the electrode 130, through the electrically conductive liquid 140, to tissue outside the body. The paths of ionic transport are designated by arrows 142 in FIG. 13A.

Preferably, the liquid 140 possesses a low resistivity to decrease ohmic loses, and thus ohmic heating effects, within the body 128. The composition of the electrically conductive liquid 140 can vary. In the illustrated and preferred embodiment, the liquid 140 comprises a hypertonic saline solution, having a sodium chloride concentration at or near saturation, which is about 9% weight by volume. Hypertonic saline solution has a low resistivity of only about 5 ohm.cm, compared to blood resistivity of about 150 ohm.cm and myocardial tissue resistivity of about 500 ohm-cm.

Alternatively, the composition of the electrically conductive liquid 140 can comprise a hypertonic potassium chloride solution. This medium, while promoting the desired ionic transfer, requires closer monitoring of the rate at which ionic transport 142 occurs through the pores, to prevent potassium overload. When hypertonic potassium chloride solution is used, it is preferred to keep the ionic transport rate below about 10 mEq/min. The imaging probe 124 is also located within the body 128. As before described, the probe 124 includes a flexible body 36, which extends through a central bore 38 and a hemostatic valve (not shown) at the distal end of the catheter tube 12. The body 36 has a distal region 40 that projects beyond the distal end 16 of the catheter tube 12 into the interior of the support structure 20. The distal body region 40 carries an IAE 150, which is sealed from the surrounding liquid 140, for example, within a housing. Like IAE 50 before described, the IAE 150 generates visualizing signals representing an image of objects surrounding the body 128.

As before explained in conjunction with FIG. 5A, the IAE 150 is preferably carried for forward and rearward movement by pushing or pulling upon the body 36. The IAE 150 is also preferably movable transverse of the body axis by the provision of a steering mechanism 76 in the distal region 40, as already described.

The IAE 150 can be variously constructed, depending upon the transparency of the body 128 to imaging energy.

For example, if the body 128 is transparent to optical energy, the IAE 150 can comprise a fiber optic channel, as already generally described (see FIG. 7 or FIG. 25). Regenerated cellulose membrane materials, typically used for blood oxygenation, dialysis, or ultrafiltration, can be made to be optically transparent. Regenerated cellulose is electrically non-conductive; however, the pores of this material (typically having a diameter smaller than about 0.1 $\mu$m) allow effective ionic transport 142 in response to the applied RF field. At the same time, the relatively small pores prevent transfer of macromolecules through the body 128, so that pressure driven liquid perfusion through the pores 129 is less likely to accompany the ionic transport 142, unless relatively high pressure conditions develop within the body 128.

Regenerated cellulose is also transparent to ultrasonic energy. The IAE 50 can thus alternatively comprise an ultrasonic transducer crystal, as also already described (see FIG. 6).

Other porous materials, which are either optically transparent or otherwise transparent to the selected imaging energy, can be used for the body 128. Candidate materials having pore sizes larger than regenerated cellulous material, such as nylon, polycarbonate, polyvinylidene fluoride (PTFE), polyethersulfone, modified acrylic copolymers, and cellulose acetate, are typically used for blood microfiltration and oxygenation. Porous or microporous materials may also be fabricated by weaving a material (such as nylon, polyester, polyethylene, polypropylene, fluorocarbon, fine diameter stainless steel, or other fiber) into a mesh having the desired pore size and porosity. These materials permit effective passage of ions in response to the applied RF field. However, as many of these materials possess larger pore diameters, pressure driven liquid perfusion, and the attendant transport of macromolecules through the pores, are also more likely to occur at normal inflation pressures for the body 128. Considerations of overall porosity, perfusion rates, and lodgment of blood cells within the pores of the body 128 must be taken more into account as pore size increase.

Low or essentially no liquid perfusion through the porous body 128 is preferred. Limited or essentially no liquid perfusion through the porous body 128 is beneficial for several reasons. First, it limits salt or water overloading, caused by transport of the hypertonic solution into the blood pool. This is especially true, should the hypertonic solution include potassium chloride, as observed above. Furthermore, limited or essentially no liquid perfusion through the porous body 128 allows ionic transport 142 to occur without disruption. When undisturbed by attendant liquid perfusion, ionic transport 142 creates a continuous virtual electrode at the body 128-tissue interface. The virtual electrode efficiently transfers RF energy without need for an electrically conductive metal surface.

As shown in FIG. 13A, the porous body 128 serves a dual purpose. Like the structure 20, the porous body 128 keeps open the interior chamber or passages within the patient's body targeted for imaging, while at the same time keeping tissue T away from potential occluding contact with the IAE 150. The body 128 also helps to stabilize the position of the IAE 50. In these ways, the body 128, like the support structure 20, provides a substantially stationary platform for visualizing tissue and anatomic structures for diagnostic purposes, making possible the creation of an accurate image of the targeted body cavity.

Furthermore, through the ionic transfer 142 of the RF field generated within the body 128, the porous body 128 also serves the therapeutic function as a tissue ablation element. The use of a porous body 128, expanded after introduction to an enlarged diameter (see FIG. 13A), makes possible the creation of larger lesions in a controlled fashion to ablate epicardial, endocardial, or intramural VT substrates. By also controlling the porosity, and thus the electrical resistivity of the body 128, the physician can significantly influence the depth of the lesion. The use of a low-resistivity body 128 results in deeper lesions, and vice versa.

Further details of the use of porous bodies to deliver ablation energy through ionic transport are found in copending patent application Ser. No. 08/631,356, filed Apr. 12, 1996 and entitled "Tissue Heating and Ablation Systems and Methods Using Electrode Structures With Distally Oriented Porous Regions," which is incorporated herein by reference.

In an alternative embodiment, the porous body 128 and IAE 150 can themselves occupy the interior of a multiple spline support structure 146, as shown in FIG. 14. In this arrangement, the exterior multiple spline structure 146 provides added stabilization and protection for the porous body and IAE 150. As shown in FIG. 14, the multiple spline support structure 146 may also carry an array of electrodes 148. These electrodes 148 can be used for mapping or characterizing tissue or for guidance of the interior porous ablation body and IAE 150, in the manners previously described.

(iii) Long Lesions

Atrial geometry, atrial anisotropy, and histopathologic changes in the left or right atria can, alone or together, form anatomic obstacles. The obstacles can disrupt the normally uniform propagation of electrical impulses in the atria, resulting in abnormal, irregular heart rhythm, called atrial fibrillation.

U.S. patent application Ser. No. 08/566,291, filed Dec. 1, 1995, and entitled "Systems and Methods for Creating Complex Lesion Patterns in Body Tissue" discloses catheter-based systems and methods that create complex long lesion patterns in myocardial tissue. In purpose and effect, the systems and methods emulate the open heart maze procedure, but do not require costly and expensive open heart surgery. These systems and methods can be used to perform other curative procedures in the heart as well.

The multiple spline support structure 152 shown in FIG. 15 is well suited for therapeutic use in the atrial regions of the heart. In FIG. 15, a transeptal deployment is shown, from the right atrium (RA), through the septum (S), into the left atrium (LA), where the support structure 152 is located for use.

The longitudinal splines 154 carry an array of electrodes 156. The electrodes 156 serve as transmitters of ablation energy. An IAE 50, as previously described, is movably carried within the interior of the structure 152.

The electrodes 156 are preferably operated in a uni-polar mode, in which the radio frequency ablation energy transmitted by the electrodes 156 is returned through an indifferent patch electrode 158 externally attached to the skin of the patient. Alternatively, the electrodes 156 can be operated in a bi-polar mode, in which ablation energy emitted by one or more electrodes 156 is returned an adjacent electrode 156 on the spline 154.

The size and spacing of the electrodes 156 shown in FIG. 15 are purposely set for creating continuous, long lesion patterns in tissue. FIG. 18 shows a representative long, continuous lesion pattern 160, which is suited to treat atrial fibrillation. Continuous, long lesion patterns 160 are formed due to additive heating effects when RF ablation energy is applied in a uni-polar mode simultaneously to the adjacent electrodes 156, provided the size and spacing requirements are observed. The additive heating effects cause the lesion pattern 160 to span adjacent, spaced apart electrodes 156, creating the desired elongated geometry, shown in FIG. 18. The additive heating effects will also occur when the electrodes 156 are operated simultaneously in a bipolar mode between electrodes 156, again provided the size and spacing requirements are observed.

The additive heating effects between spaced apart electrodes 156 intensify the desired therapeutic heating of tissue contacted by the electrodes 156. The additive effects heat the tissue at and between the adjacent electrodes 156 to higher temperatures than the electrodes 156 would otherwise heat the tissue, if conditioned to individually transit energy to the tissue, or if spaced apart enough to prevent additive heating effects.

When the spacing between the electrodes 156 is equal to or less than about 3 times the smallest of the diameters of the electrodes 156, the simultaneous emission of energy by the electrodes 156, either bipolar between the segments or unipolar to the indifferent patch electrode, creates the elongated continuous lesion pattern 160 shown in FIG. 18 due to the additive heating effects. Conversely, when the spacing between the electrodes 156 is greater than about 5 times the smallest of the diameters of the electrodes 156, the simultaneous emission of energy by the electrodes 156, either bipolar between segments or unipolar to the indifferent patch electrode, does not generate additive heating effects. Instead, the simultaneous emission of energy by the electrodes 156 creates an elongated segmented, or interrupted, lesion pattern 162 in the contacted tissue area, as shown in FIG. 20.

Alternatively, when the spacing between the electrodes 156 along the contacted tissue area is equal to or less than about 2 times the longest of the lengths of the electrodes 156, the simultaneous application of energy by the electrodes 156, either bipolar between electrodes 156 or unipolar to the indifferent patch electrode, also creates an elongated continuous lesion pattern 160 (FIG. 18) due to additive heating effects. Conversely, when the spacing between the electrodes 156 along the contacted tissue area is greater than about 3 times the longest of the lengths of the electrodes 156, the simultaneous application of energy, either bipolar between electrodes 156 or unipolar to the indifferent patch electrode, creates an elongated segmented, or interrupted, lesion pattern 162 (FIG. 20).

In an alternative embodiment (see FIG. 15), the assembly includes periodic bridge splines 164. The bridge splines 164 are soldered or otherwise fastened to the adjacent longitudinal splines 154. The bridge splines 164 carry electrodes 166, or are otherwise made to transmit ablation energy by exposure of electrically conductive material. Upon transmission of ablation energy, the bridge splines 166 create long transverse lesion patterns 168 (see FIG. 19) that span across the long longitudinal lesion patterns 160 created by the adjacent splines 154. The transverse lesions 168 link the longitudinal lesions 160 to create complex lesion patterns that emulate the patterns formed by incisions during the surgical maze procedure.

Further details of the creation of complex long lesion patterns in the treatment of atrial fibrillation are found in copending U.S. application Ser. No. 08/566,291, filed Dec. 1, 1995, and entitled "Systems and Methods for Creating Complex Lesion Patterns in Body Tissue," which is incorporated herein by reference.

B. Lesion Visualization

The IAE 50/150 associated with the structures shown permits the physician to visually inspect the lesion pattern during or after ablation to confirm that the desired pattern and depth have been created. By manipulating the IAE 50/150 in the manner described above during or after ablation, the physician can view the lesions from different directions, to assure that the lesion geometry and depth conforms to expectations. The IAE 50/150 can also inspect a long lesion pattern (like patterns 160 or 168 in FIG. 19) during or after ablation for gaps or interruptions, which could, if present, provide unwanted pathways for aberrant electrical pulses. Contrast echocardiography, employing contrast media (as earlier described in conjunction with FIG. 8), may also be used to identify gaps in long lesions during or after their formation. Since perfusion through thermally destroyed tissue is significantly less than in other tissue, gaps in long lesion patterns (i.e., tissue that has not been thermally destroyed) will, in the presence of contrast media, appear ultrasonically "brighter" than tissue in the lesion area. Ablation of these gaps, once identified by the IAE 50/150, completes the long lesion pattern to assure that the intended therapeutic result is achieved.

The IAE 50/150 can also help the physician measure the width, length, and depth of the lesion pattern. Using the IAE 50/150, the physician can directly measure these physical lesion characteristics, instead of or as an adjunct to predicting such characteristics from measurements of applied power, impedance, tissue temperature, and ablation time.

The IAE 50/150 can further help the physician characterize tissue morphology. Using the IAE 50/150, the physician can visualize border regions between healthy and infarcted tissue, alone or in combination with electrical impulse sensing with the electrodes 156.

Various features of the invention are set forth in the following claims.

We claim:

1. A system for imaging an interior body region comprising a probe including an axis and an imaging structure having a periphery adapted to selectively assume an expanded geometry and a collapsed geometry, and an array of spaced apart ultrasound transducers attached to the periphery of the imaging structure, wherein members of the array move radially outward and inward relative to the axis as the periphery assumes the expanded geometry and the collapsed geometry respectively.

2. A system according to claim 1 wherein the imaging structure comprises at least two spaced apart support members.

3. A system according to claim 2 wherein the support members are made from metal material.

4. A system according to claim 3 wherein the metal material includes nickel titanium.

5. A system according to claim 3 wherein the metal material includes stainless steel.

6. An assembly according to claim 2 wherein the support members are made from plastic material.

7. A system according to claim 2 wherein the support members comprise elongated spline elements assembled in a circumferentially spaced relationship.

8. A system according to claim 1 wherein the imaging structure includes support members and is adapted to assume the collapsed geometry in response to external force, the imaging structure being urged by the support members toward the expanded geometry in the absence of the force.

9. A system according to claim 8 and further including a sheath slidable relative to the imaging structure in a first direction to apply external force to urge the support elements into the collapsed geometry and in a second direction to release the external force, thereby allowing the support structure to assume an expanded geometry.

10. A system according to claim 1 wherein the imaging structure comprises a three-dimensional structure.

11. A system according to claim 10 wherein the three-dimensional structure comprises an expandable body.

12. A system according to claim 11 wherein the expandable body expands to an expanded geometry in response to fluid pressure.

13. A system according to claim 11 wherein the expandable body collapses in the absence of fluid pressure.

14. A system according to claim 1 wherein the array comprises a phased array ultrasound transducer assembly.

15. A system according to claim 1 wherein the array comprises coatings each comprising either an ultrasound transducer material or an ultrasound transducer material composite deposited in a spaced apart relationship on the periphery of the imaging structure.

16. A system according to claim 15 wherein the coatings are deposited by a technique including either ion beam assisted deposition, or vapor deposition, or sputtering.

17. A system according to claim 1 wherein the array comprises preformed elements each comprising either an ultrasound transducer material or an ultrasound transducer material composite secured in a spaced apart relationship on the periphery of the imaging structure.

18. A system according to claim 1 and further including a support structure extending beyond the periphery of the imaging structure.

19. A system according to claim 18 and further including at least one electrode carried by the support structure.

20. A system according to claim 18 and further including a steering element coupled to the imaging structure to move the structure relative to the support structure.

21. A system according to claim 20 wherein the support structure has an axis, and wherein the steering element moves the imaging structure along the axis.

22. A system according to claim 20 wherein the support structure has an axis, and wherein the steering element moves the imaging structure transverse to the axis.

23. A system according to claim 20 wherein the support structure has an axis, and wherein the steering element rotates the imaging structure about the axis.

24. A system according to claim 20 wherein the steering element includes an actuator to move the imaging structure in response to control commands.

25. A system according to claim 20 and further including a steering element coupled to the imaging element to move the imaging structure without moving the support structure.

26. A method for visualizing body tissue comprising the steps of providing a probe with an imaging structure having a periphery adapted to selectively assume an expanded geometry and a collapsed geometry, and an array of spaced apart ultrasound transducers attached to the periphery of the imaging structure, guiding the probe into an interior body region while causing the imaging structure to assume the collapsed geometry, causing the imaging structure to assume the expanded geometry upon arrival in the interior body region, and operating the imaging structure, while in the expanded geometry, to visualize tissue in the interior body region.

27. A method according to claim 26 and further including the step of generating an image of tissue visualized by the imaging structure.

28. A method according to claim 27 and further including the step of using the image to orient the imaging structure.

29. A method according to claim 27 and further including the step of using the image to view a lesion.

30. A method according to claim 27 and further including the step of using the image to assess contact between the imaging structure and surrounding tissue.

31. A method according to claim 27 and further including the step of using the image to identify thrombus.

32. A method according to claim 27 and further including the step of using the image to characterize tissue morphology.

33. A method according to claim 26 wherein the introducing step includes introducing the imaging structure into a heart chamber.

34. A method according to claim 26 and further including the step of moving the imaging structure.

35. A method according to claim 26 and further including the step of moving the imaging element within a support structure that extends beyond the periphery of the imaging structure.

36. A method according to claim 26 and further including the step of moving the imaging structure within a support structure that extends beyond the periphery of the imaging structure, the imaging structure being moved without moving the support structure.

37. A method according to claim 36 wherein the operating step acquires image slices during the moving step.

38. A system for imaging an interior body region, comprising
a probe having an imaging structure adapted to selectively assume an expanded geometry and a collapsed geometry, and
an array of ultrasound transducers on the imaging structure, wherein members of the array move away from one another as the imaging structure assumes the expanded geometry.

39. The system of claim 38, wherein the imaging structure comprises an expandable body.

40. The system of claim 39, wherein the expandable body includes a plurality of spline elements arranged to have a predetermined geometry in the expanded condition.

41. The system of claim 40, wherein the array of ultrasound transducers comprises an ultrasound transducer on each of the spline elements.

42. The system of claim 39, wherein the expandable body assumes the expanded geometry in response to internal fluid pressure.

43. The system of claim 38, wherein the array of ultrasound transducers comprises a phased array ultrasound transducer assembly.

44. The system of claim 38, wherein the array of ultrasound transducers includes transducer material deposited on the imaging structure by ion beam assisted deposition.

45. The system of claim 38, further comprising a support structure surrounding the imaging structure.

46. A system for imaging an interior body region, comprising
a probe including a distal portion,
an imaging structure having a predetermined geometry on the distal portion,
a plurality of arrays of ultrasound transducers attached to the imaging structure in a predetermined arrangement for acquiring images along a plurality of sectors, and
a support structure on the probe and substantially surrounding the imaging structure, the support structure being adapted to assume an expanded geometry and a collapsed geometry.

47. The system of claim 46, wherein the probe includes a longitudinal axis, and wherein the support structure expands radially with respect to the longitudinal axis as it assumes the expanded geometry.

48. The system of claim 46, wherein the imaging structure is an expandable body adapted to assume an expanded geometry and a collapsed geometry.

49. The system of claim 48, wherein the plurality of arrays comprises a plurality of phased arrays of ultrasound transducers disposed on the imaging structure and adapted to move away from one another as the imaging structure assumes the expanded geometry.

50. The system of claim 46, wherein the imaging structure has a fixed predetermined geometry for supporting the plurality of arrays in the predetermined arrangement.

51. The system of claim 50, wherein the imaging structure comprises a hemispherical body or a cylindrical body.

* * * * *